US012727749B2

(12) United States Patent
Igarashi

(10) Patent No.: US 12,727,749 B2
(45) Date of Patent: Sep. 8, 2026

(54) MEDICAL OBSERVATION SYSTEM, MEDICAL IMAGING DEVICE AND IMAGING METHOD

(71) Applicant: OLYMPUS CORPORATION, Tokyo (JP)

(72) Inventor: Takaaki Igarashi, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 945 days.

(21) Appl. No.: 17/902,031

(22) Filed: Sep. 2, 2022

(65) Prior Publication Data

US 2023/0000330 A1 Jan. 5, 2023

Related U.S. Application Data

(63) Continuation of application No. PCT/JP2020/009883, filed on Mar. 6, 2020.

(51) Int. Cl.
*A61B 1/06* (2006.01)
*A61B 1/00* (2006.01)
(Continued)

(52) U.S. Cl.
CPC ........ *A61B 1/0638* (2013.01); *A61B 1/00009* (2013.01); *A61B 1/000095* (2022.02);
(Continued)

(58) Field of Classification Search
None
See application file for complete search history.

(56) References Cited

U.S. PATENT DOCUMENTS

2005/0148834 A1* 7/2005 Hull ..................... A61B 5/0059 600/317
2007/0276259 A1* 11/2007 Okawa ................. A61B 5/0084 600/476

(Continued)

FOREIGN PATENT DOCUMENTS

CN 105244804 A 1/2016
CN 108135454 A 6/2018

(Continued)

OTHER PUBLICATIONS

International Search Report dated Apr. 14, 2020 issued in PCT/JP2020/009883.
English Abstract of JP 2012-130629 A dated Jul. 12, 2012.

*Primary Examiner* — Mohammed Jebari
(74) *Attorney, Agent, or Firm* — Scully, Scott, Murphy & Presser, P.C.

(57) ABSTRACT

A medical observation system includes: a light source configured to emit, to body tissue, at least one of first narrow band light and second narrow band light; an imaging element that includes: a pixel portion including plural pixels arranged in a two-dimensional matrix; and a color filter including red filters, green filters, and blue filters that are provided on light receiving surfaces of the plural pixels, each of the light receiving surfaces including any one filter of the red, green, and blue filters on each of the light receiving surfaces; and a cut filter that is provided on a light receiving surface side of at least the pixels provided with the green filters, the cut filter being configured to shield light of a shorter wavelength band including the wavelength band of the second narrow band light, and transmit therethrough the first narrow band light.

14 Claims, 28 Drawing Sheets

(51) Int. Cl.

*A61B 1/04* (2006.01)
*A61B 1/045* (2006.01)
*H04N 23/50* (2023.01)
*H04N 23/56* (2023.01)

(52) U.S. Cl.

CPC .......... *A61B 1/00186* (2013.01); *A61B 1/043* (2013.01); *A61B 1/044* (2022.02); *A61B 1/045* (2013.01); *A61B 1/063* (2013.01); *A61B 1/0655* (2022.02); *H04N 23/555* (2023.01); *H04N 23/56* (2023.01)

(56) References Cited

U.S. PATENT DOCUMENTS

2008/0050013 A1* 2/2008 Munro .................... G01S 17/87 382/154
2010/0003664 A1* 1/2010 Reinisch .............. A61B 5/0071 435/288.7
2012/0130175 A1* 5/2012 Koshikawa .......... A61B 1/0638 600/178
2012/0154567 A1 6/2012 Yamaguchi et al.
2015/0088001 A1* 3/2015 Lindvold ............. G02B 6/0008 600/478
2015/0099932 A1* 4/2015 Morimoto .............. H05B 45/12 315/153
2016/0192834 A1* 7/2016 Niida ................. A61B 1/00009 600/109
2016/0265747 A1* 9/2016 Nagao .................. A61B 1/0684
2017/0258296 A1* 9/2017 Kaku ..................... A61B 1/044
2017/0289467 A1* 10/2017 Yamamoto ............. G02B 5/208
2018/0220881 A1 8/2018 Adachi
2019/0282135 A1* 9/2019 Ito .......................... A61B 1/044
2019/0343384 A1* 11/2019 Plaian ...................... A61B 3/12
2020/0288965 A1* 9/2020 Gamliel .................... G06T 5/94
2021/0035276 A1* 2/2021 Ago .......................... G06T 7/62
2021/0058591 A1* 2/2021 Takashima ............. H04N 25/17
2021/0076921 A1* 3/2021 Nagae .................. A61B 1/0005
2021/0097331 A1* 4/2021 Kamon .................. H04N 7/183
2021/0208075 A1* 7/2021 Roberts .................. G01N 21/64
2021/0266508 A1* 8/2021 Deguchi ............... G06T 11/001
2022/0110526 A1* 4/2022 Gamliel ............... A61B 5/0071
2022/0273165 A1* 9/2022 Ouyang ............... A61B 1/0646
2022/0296090 A1* 9/2022 Ouyang ............. A61B 1/00103

FOREIGN PATENT DOCUMENTS

JP 2011200534 A 10/2011
JP 2012125501 A 7/2012
JP 5371946 B2 12/2013

* cited by examiner

FIG.7A
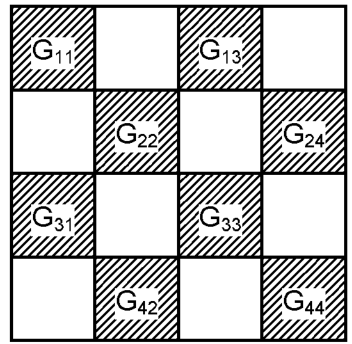
FIG.7B
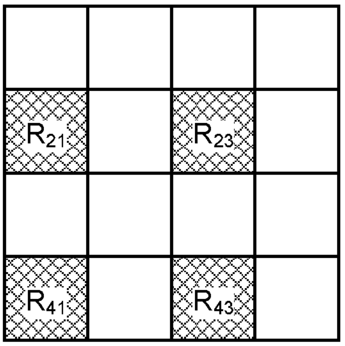
FIG.7C
$B_{12}$
$B_{14}$
$B_{32}$
$B_{34}$

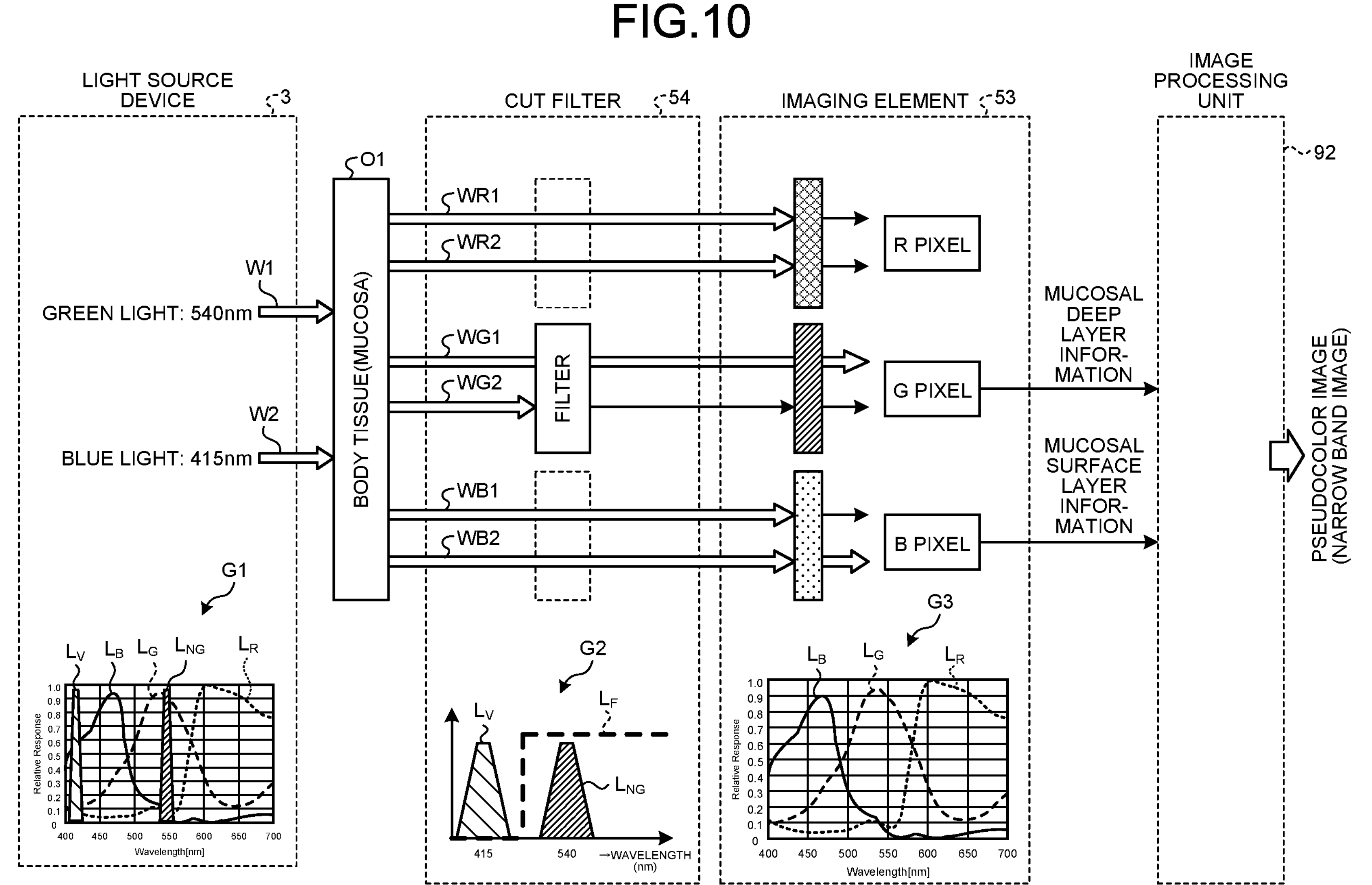
FIG.10
LIGHT SOURCE DEVICE
3
W1
GREEN LIGHT: 540nm
W2
BLUE LIGHT: 415nm
G1
$L_V$
$L_B$
$L_G$
$L_{NG}$
$L_R$
Relative Response
Wavelength[nm]
O1
BODY TISSUE(MUCOSA)
CUT FILTER
54
WR1
WR2
WG1
WG2
FILTER
WB1
WB2
G2
$L_V$
$L_F$
$L_{NG}$
415
540
→WAVELENGTH (nm)
IMAGING ELEMENT
53
R PIXEL
G PIXEL
B PIXEL
G3
$L_B$
$L_G$
$L_R$
Relative Response
Wavelength[nm]
MUCOSAL DEEP LAYER INFOR-MATION
MUCOSAL SURFACE LAYER INFOR-MATION
IMAGE PROCESSING UNIT
92
PSEUDOCOLOR IMAGE (NARROW BAND IMAGE)

LIGHT SOURCE DEVICE
3
O3
CUT FILTER
54
IMAGING ELEMENT
53
IMAGE PROCESSING UNIT
92
WF10
WR20
R PIXEL
W2
EXCITATION LIGHT: 415nm
WF10
WG20
FILTER
G PIXEL
FIRST NECES-SARY COM-PONENT
WF10
WB20
B PIXEL
FIRST FRAME
SEC-OND FRAME
BODY TISSUE
PSEUDOCOLOR IMAGE
(AUTOFLUORESCENCE IMAGE)
WR30
R PIXEL
W1
REFERENCE LIGHT: 540nm
WG30
FILTER
G PIXEL
SECOND NECES-SARY COM-PONENT
WB30
B PIXEL

FIG.13

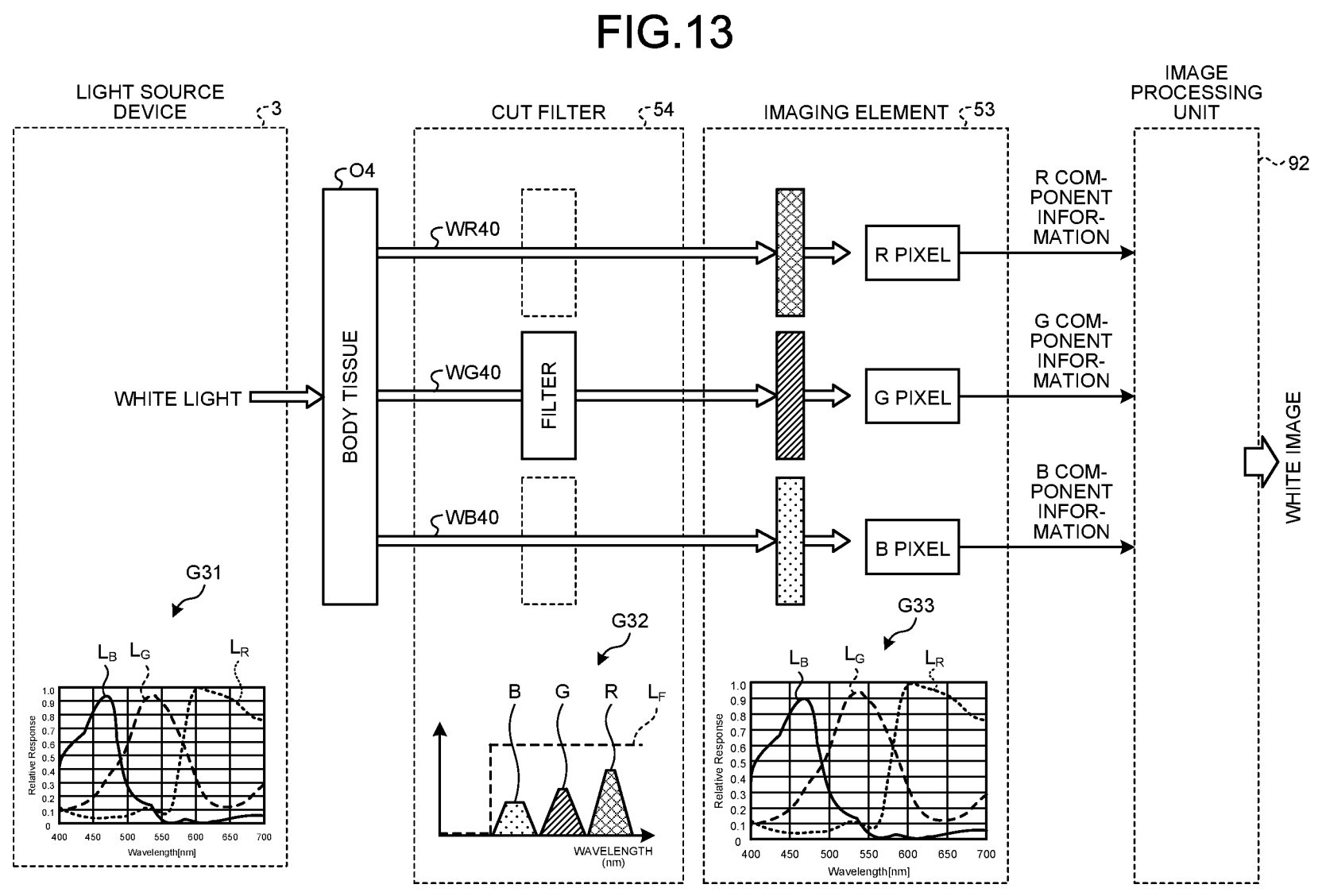

LIGHT SOURCE DEVICE
3
WHITE LIGHT
G31
$L_B$
$L_G$
$L_R$
Relative Response
Wavelength[nm]
O4
BODY TISSUE
CUT FILTER
54
WR40
WG40
WB40
FILTER
G32
B
G
R
$L_F$
WAVELENGTH (nm)
IMAGING ELEMENT
53
R PIXEL
G PIXEL
B PIXEL
G33
$L_B$
$L_G$
$L_R$
Relative Response
Wavelength[nm]
R COMPONENT INFORMATION
G COMPONENT INFORMATION
B COMPONENT INFORMATION
IMAGE PROCESSING UNIT
92
WHITE IMAGE

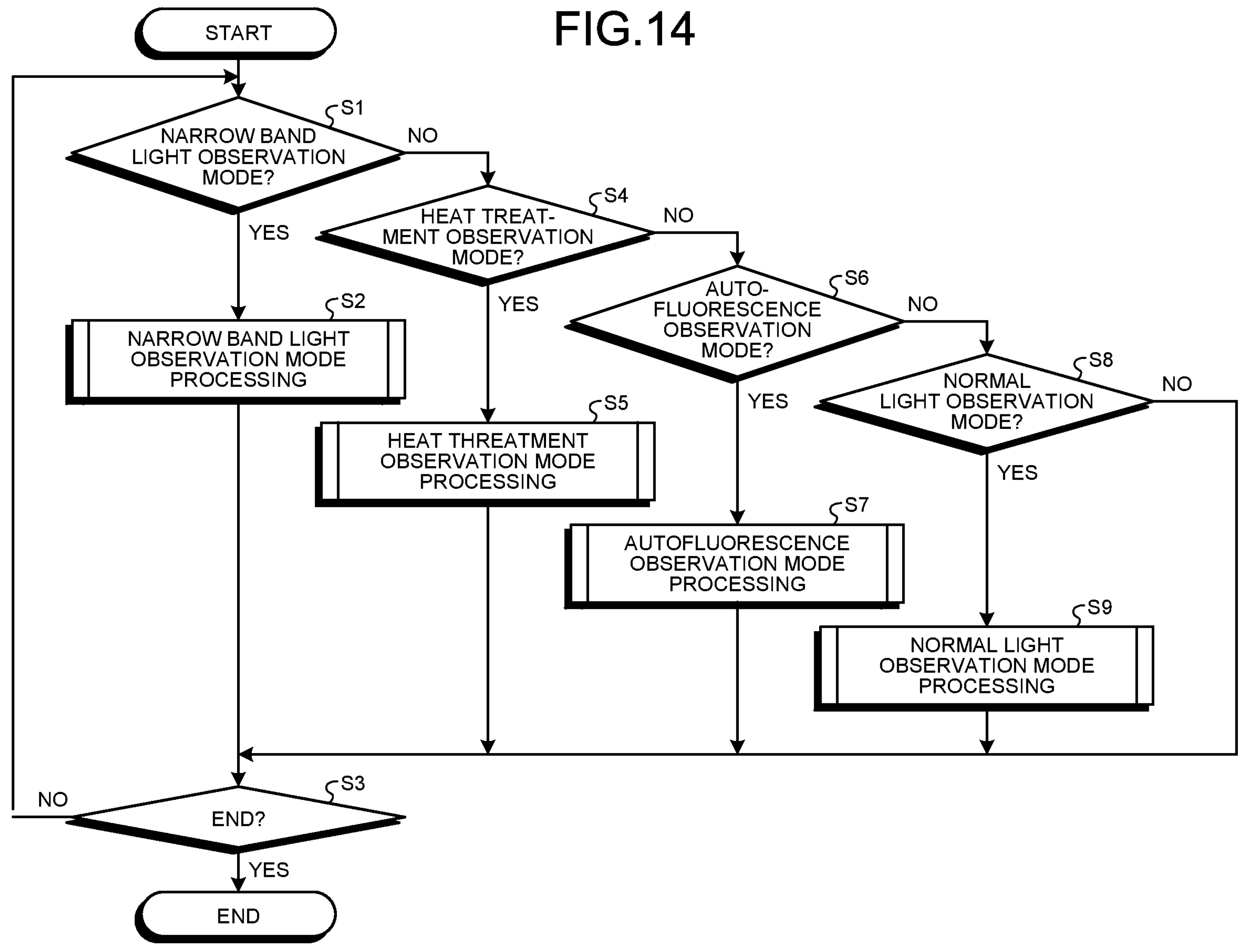
FIG.14
START
NARROW BAND LIGHT OBSERVATION MODE?
S1
NO
YES
HEAT TREAT-MENT OBSERVATION MODE?
S4
NO
YES
AUTO-FLUORESCENCE OBSERVATION MODE?
S6
NO
YES
NORMAL LIGHT OBSERVATION MODE?
S8
NO
YES
NARROW BAND LIGHT OBSERVATION MODE PROCESSING
S2
HEAT THREATMENT OBSERVATION MODE PROCESSING
S5
AUTOFLUORESCENCE OBSERVATION MODE PROCESSING
S7
NORMAL LIGHT OBSERVATION MODE PROCESSING
S9
END?
S3
NO
YES
END

FIG.20

MEDICAL OBSERVATION SYSTEM, MEDICAL IMAGING DEVICE AND IMAGING METHOD

CROSS-REFERENCE TO RELATED APPLICATION

This application is a continuation of International Application No. PCT/JP2020/009883, filed on Mar. 6, 2020, the entire contents of which are incorporated herein by reference.

BACKGROUND

1. Technical Field

The present disclosure relates to a medical observation system, a medical imaging device, and an imaging method that generate image data on an object, such as a subject, by imaging the object.

2. Related Art

In the related art, two imaging elements are provided in an endoscope, light for emission is switched between first narrow band light and second narrow band light having wavelength bands different from each other according to observation modes, and one of the two imaging elements is caused to perform imaging correspondingly to an observation mode (see, for example, Japanese Patent No. 5371946). When narrow band light observation is performed using this technique, imaging is performed by a first imaging element through irradiation of a subject with the first narrow band light, the first imaging element including, on a light receiving surface thereof, a light shielding filter that blocks reflected light from the subject at a predetermined light shielding rate. According to Japanese Patent No. 5371946, when first autofluorescence light observation is performed, first autofluorescence emitted from the subject by irradiation of the subject with the first narrow band light serving as excitation light is imaged by the first imaging element via the light shielding filter, and in a second autofluorescence light observation mode, second autofluorescence emitted from the subject by irradiation of the subject with the second narrow band light serving as excitation light is imaged by a second imaging element.

SUMMARY

In some embodiments, a medical observation system includes: a light source configured to emit, to body tissue, at least one of: first narrow band light having a wavelength band narrower than a wavelength band of white light; and second narrow band light that has a wavelength band shorter than the wavelength band of the first narrow band light and causes excitation of an advanced glycation end product produced by performing a heat treatment on the body tissue; an imaging element that includes: a pixel portion including plural pixels arranged in a two-dimensional matrix; and a color filter including red filters, green filters, and blue filters that are provided on light receiving surfaces of the plural pixels, each of the light receiving surfaces including any one filter of the red, green, and blue filters on each of the light receiving surfaces, the imaging element being configured to generate image data by imaging at least one of returned light from the body tissue and fluorescence from the advanced glycation end product; and a cut filter that is provided on a light receiving surface side of at least the pixels provided with the green filters, the cut filter being configured to shield light of a shorter wavelength band including the wavelength band of the second narrow band light, and transmit therethrough the first narrow band light.

In some embodiments, provided is a medical observation system equipped with a narrow band light observation mode and a heat treatment observation mode. The medical observation system includes: a light source configured to illuminate body tissue with: blue light that is to illuminate the body tissue in the narrow band light observation mode, is highly absorbed by hemoglobin in blood, and is easily reflected by a mucosal surface layer; and blue light that is to illuminate the body tissue in the heat treatment observation mode and excites an advanced glycation end product generated by performing a heat treatment on the body tissue; an imaging element to be commonly used in the narrow band light observation mode and the heat treatment observation mode, the imaging element including: a pixel portion including plural pixels arranged in a two-dimensional matrix; and a color filter including red filters, green filters, and blue filters that are provided on light receiving surfaces of the plural pixels, each of the light receiving surfaces including any one filter of the red, green, and blue filters on each of the light receiving surfaces, the imaging element being configured to generate image data by imaging at least one of returned light from the body tissue and fluorescence from the advanced glycation end product; and a cut filter that is provided on a light receiving surface side of at least the pixels provided with the green filters, the cut filter being configured to shield light of a wavelength band including a wavelength band of the fluorescence, and transmit therethrough the blue light.

In some embodiments, a medical imaging device includes: an imaging element including: a pixel portion including plural pixels arranged in a two-dimensional matrix; and a color filter including red filters, green filters, and blue filters that are provided on light receiving surfaces of the plural pixels, each of the light receiving surfaces including any one filter of the red, green, and blue filters on each of the light receiving surfaces; and a cut filter provided on a light receiving surface side of at least the pixels provided with the green filters, the imaging element being configured to generate image data by imaging at least one of: returned light from body tissue when first narrow band light having a wavelength band narrower than a wavelength band of white light has been emitted to the body tissue; and fluorescence from an advanced glycation end product generated by performing a heat treatment on the body tissue when second narrow band light that excites the advanced glycation end product has been emitted to the advanced glycation end product, the second narrow band light having a wavelength band shorter than the wavelength band of the first narrow band light, and the cut filter being configured to shield light having a shorter wavelength band including a wavelength band of the second narrow band light and transmit therethrough the first narrow band light.

In some embodiments, a medical imaging device includes: an imaging element including: a pixel portion including plural pixels arranged in a two-dimensional matrix; and a color filter including red filters, green filters, and blue filters that are provided on light receiving surfaces of the plural pixels, each of the light receiving surfaces including any one filter of the red, green, and blue filters on each of the light receiving surfaces, the imaging element being configured to generate image data by imaging at least one of: returned light from body tissue when first narrow band light having a wavelength band narrower than a wavelength band of white light has been emitted to the body tissue; and fluorescence from an advanced glycation end product generated by performing a heat treatment on the body tissue when second narrow band light that excites the advanced glycation end product has been emitted to the advanced glycation end product, the second narrow band light having a wavelength band shorter than the wavelength band of the first narrow band light, and the green filters being configured to shield light having a shorter wavelength band including the wavelength band of the second narrow band light and transmit therethrough the first narrow band light.

In some embodiments, an imaging method includes: emitting, by a light source, narrow band light to excite an advanced glycation end product, to body tissue, capturing, by blue pixels of an imaging element, an image of first light of: returned light from the body tissue; and fluorescence from the advanced glycation end product, the first light having passed through blue filters configured to mainly transmit therethrough light of a blue wavelength band, and capturing, by green pixels of the imaging element, an image of second light of: the returned light from the body tissue; and the fluorescence from the advanced glycation end product, the second light having passed through a cut filter to shield light shorter in wavelength than the fluorescence and having passed through green filters configured to mainly transmit therethrough light of a green wavelength band.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 7A is a diagram schematically illustrating signal values of G pixels of an imaging element according to the first embodiment;

FIG. 7B is a diagram schematically illustrating signal values of R pixels of the imaging element according to the first embodiment;

FIG. 7C is a diagram schematically illustrating signal values of B pixels of the imaging element according to the first embodiment;

FIG. 10 is a diagram schematically illustrating principles of observation in a narrow band light observation mode according to the first embodiment;

FIG. 13 is a diagram schematically illustrating principles of observation in a normal light observation mode according to the first embodiment;

FIG. 14 is a flowchart illustrating an outline of processing executed by the endoscope system according to the first embodiment;

FIG. 20 is a flowchart illustrating an outline of imaging recording processing in FIG. 19;

DETAILED DESCRIPTION

Modes for implementing the present disclosure will hereinafter be described in detail, together with the drawings. The present disclosure is not limited by the following embodiments. Furthermore, the drawings referred to in the following description schematically depict shapes, sizes, and positional relations merely to an extent that allows substance of the present disclosure to be understood. That is, the present disclosure is not limited only to the shapes, sizes, and positional relations exemplified by the drawings. In addition, any portions that are the same will be assigned with the same reference sign throughout the drawings. An endoscope system including a rigid endoscope and a medical imaging device will be described as an example of a medical observation system according to the present disclosure.

First Embodiment

Configuration of Endoscope System

Figure 1:
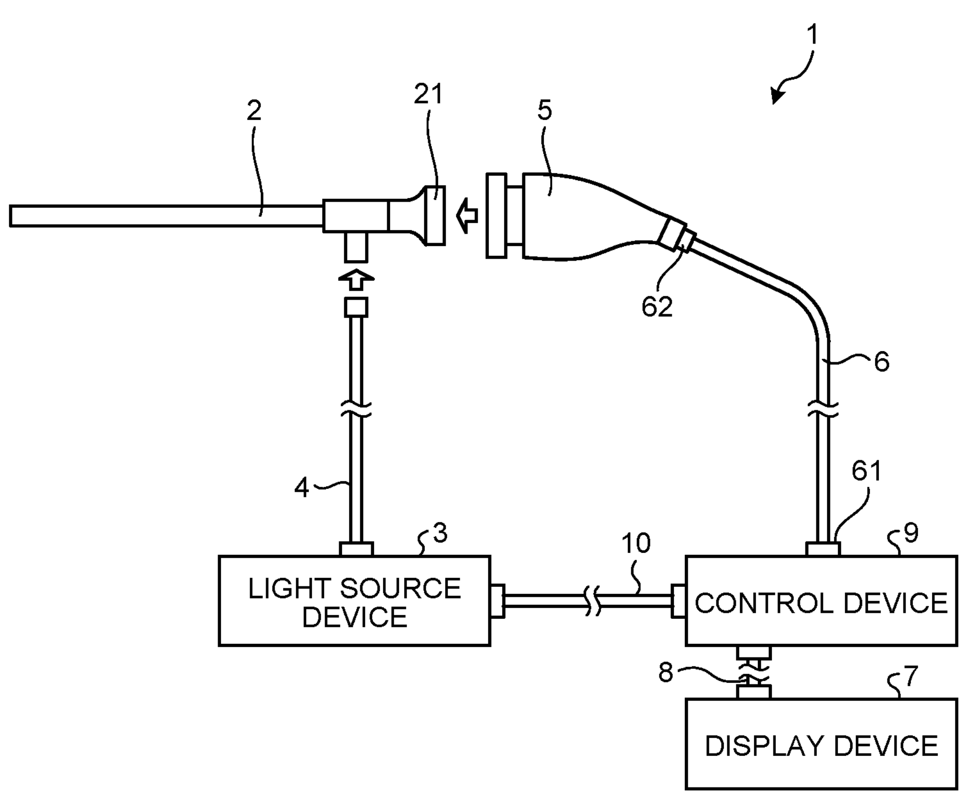
FIG. 1 is a diagram illustrating a schematic configuration of an endoscope system according to a first embodiment.

FIG. 1 is a diagram illustrating a schematic configuration of an endoscope system according to a first embodiment. An endoscope system 1 illustrated in FIG. 1 is a system that is used in the medical field and is for observation of body tissue in a subject, such as an organism. For this first embodiment, a rigid endoscope system using a rigid endoscope (an insertion portion 2) illustrated in FIG. 1 will be described as the endoscope system 1, but without being limited to the rigid endoscope system, the endoscope system 1 may be, for example, an endoscope system including a flexible endoscope. The endoscope system 1 may also be a system including a medical imaging device that captures an image of a subject and where surgery or treatment is conducted while a display image based on image data captured by this medical imaging device is being displayed by a display device. The endoscope system 1 illustrated in FIG. 1 is used when surgery or treatment of a subject is conducted by use of a treatment tool (not illustrated in the drawings), such as an electrosurgical knife or an energy device, which enables heat treatment.

The endoscope system 1 illustrated in FIG. 1 includes the insertion portion 2, a light source device 3, a light guide 4, an endoscope camera head 5 (an imaging device for an endoscope), a first transmission cable 6, a display device 7, a second transmission cable 8, a control device 9, and a third transmission cable 10.

The insertion portion 2 is rigid or at least a part of the insertion portion 2 is flexible, and the insertion portion 2 has an elongated shape. The insertion portion 2 is inserted into a subject, such as a patient, via a trocar. The insertion portion 2 has, provided therein, an optical system, such as a lens, that forms an observation image.

One end of the light guide 4 is connected to the light source device 3, and the light source device 3 supplies, under control by the control device 9, illumination light to be emitted to the interior of a subject, to that one end of the light guide 4. The light source device 3 is implemented by use of: any one or more selected from a group of a light emitting diode (LED) light source, a xenon lamp, and a semiconductor laser element, such as a laser diode (LD); a processor that is a processing device having hardware, such as a field programmable gate array (FPGA) or a central processing unit (CPU); and a memory that is a transitory storage area used by the processor. The light source device 3 and the control device 9 may be configured to perform communication individually as illustrated in FIG. 1 or may be configured to be integrated with each other.

The one end of the light guide 4 is detachably connected to the light source device 3 and the other end of the light guide 4 is detachably connected to the insertion portion 2. The light guide 4 guides the illumination light supplied from the light source device 3 to the other end from the one end, to supply the illumination light to the insertion portion 2.

An eyepiece unit 21 of the insertion portion 2 is detachably connected to the endoscope camera head 5. Under control by the control device 9, the endoscope camera head 5 generates image data (RAW data) by receiving an observation image formed by the insertion portion 2 and performing photoelectric conversion of the observation image, and outputs the image data to the control device 9 via the first transmission cable 6.

One end of the first transmission cable 6 is detachably connected to the control device 9 via a video connector 61, and the other end of the first transmission cable 6 is detachably connected to the endoscope camera head 5 via a camera head connector 62. The first transmission cable 6 transmits the image data output from the endoscope camera head 5 to the control device 9 and transmits, for example, setting data and electric power output from the control device 9, to the endoscope camera head 5. The setting data include a control signal, a synchronization signal, and a clock signal for controlling the endoscope camera head 5.

Under control by the control device 9, the display device 7 displays a display image based on the image data that have been subjected to image processing at the control device 9, and various kinds of information related to the endoscope system 1. The display device 7 is implemented by use of a display monitor of, for example, liquid crystal or organic electroluminescence (EL).

One end of the second transmission cable 8 is detachably connected to the display device 7, and the other end of the second transmission cable 8 is detachably connected to the control device 9. The second transmission cable 8 transmits the image data that have been subjected to the image processing at the control device 9, to the display device 7.

The control device 9 is implemented by use of a processor that is a processing device having hardware, such as a graphics processing unit (GPU), an FPGA, or a CPU, and a memory that is a transitory storage area used by the processor. According to a program recorded in the memory, the control device 9 integrally controls operation of the light source device 3, the endoscope camera head 5, and the display device 7, via each of the first transmission cable 6, the second transmission cable 8, and the third transmission cable 10. Furthermore, the control device 9 performs various kinds of image processing of the image data input via the first transmission cable 6 and outputs the image processed image data to the second transmission cable 8.

One end of the third transmission cable 10 is detachably connected to the light source device 3, and the other end of the third transmission cable 10 is detachably connected to the control device 9. The third transmission cable 10 transmits control data from the control device 9 to the light source device 3.

Functional Configuration of Main Parts of Endoscope System

Figure 2:
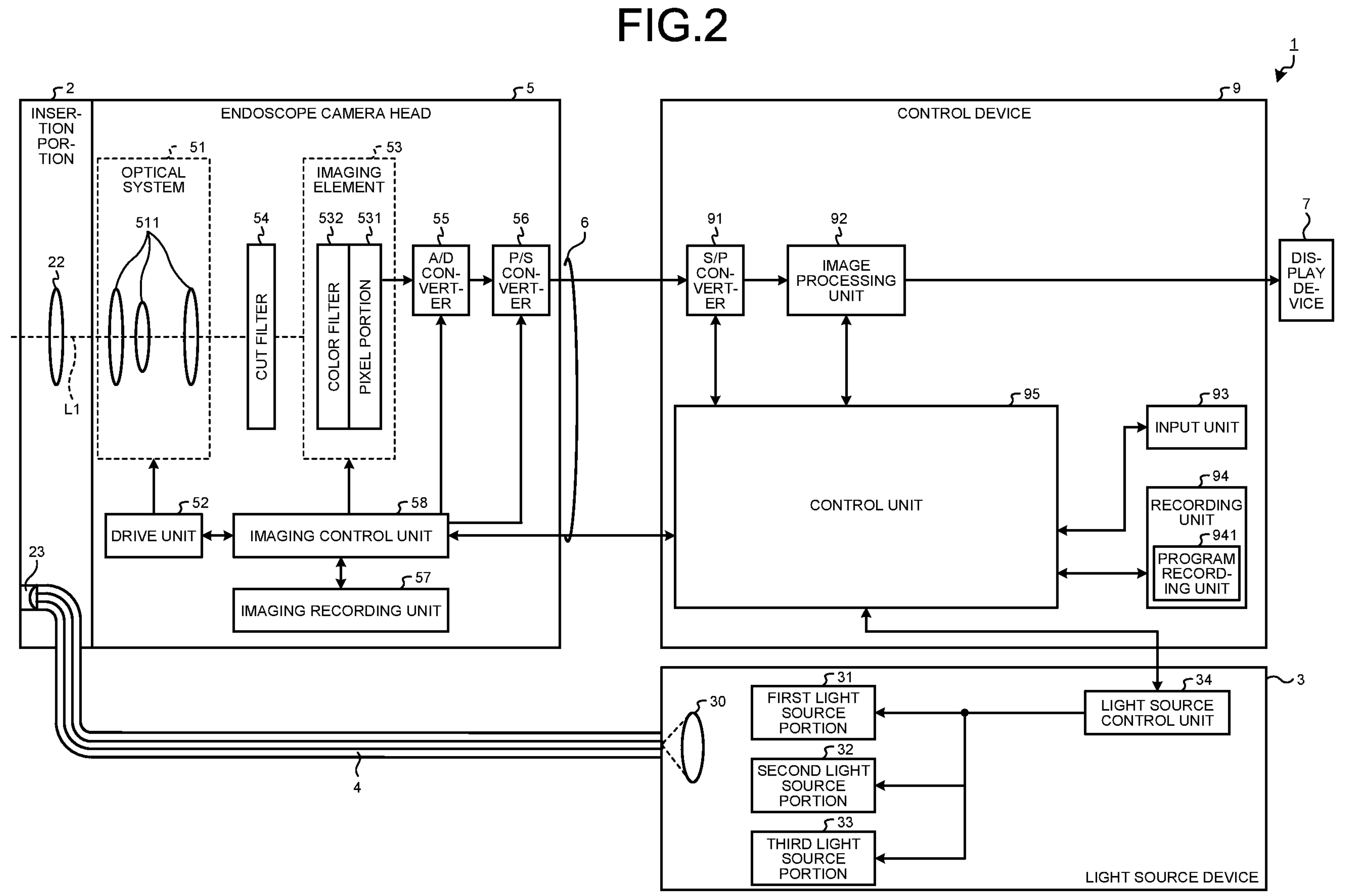
FIG. 2 is a block diagram illustrating a functional configuration of main parts of the endoscope system according to the first embodiment.

A functional configuration of main parts of the endoscope system 1 described above will be described next. FIG. 2 is a block diagram illustrating the functional configuration of the main parts of the endoscope system 1.

Configuration of Insertion Portion

A configuration of the insertion portion 2 will be described first. The insertion portion 2 includes an optical system 22 and an illumination optical system 23.

The optical system 22 forms a subject image by condensing light, such as reflected light reflected by a subject, returned light from a subject, excitation light from a subject, and/or light emitted by a subject. The optical system 22 is implemented by use of, for example, one or plural lenses.

The illumination optical system 23 outputs illumination light supplied from the light guide 4, to a subject. The illumination optical system 23 is implemented by use of, for example, one or plural lenses.

Configuration of Light Source Device

A configuration of the light source device 3 will be described next. The light source device 3 includes a condenser lens 30, a first light source portion 31, a second light source portion 32, a third light source portion 33, and a light source control unit 34.

The condenser lens 30 condenses light emitted by each of the first light source portion 31, the second light source portion 32, and the third light source portion 33 and outputs the condensed light to the light guide 4.

Under control by the light source control unit 34, the first light source portion 31 supplies illumination light that is white light to the light guide 4 by emitting white light (normal light) that is visible light. The first light source portion 31 is configured by use of, for example, a collimator lens, a white LED lamp, and a driver. The first light source portion 31 may supply visible white light by simultaneous emission using a red LED lamp, a green LED lamp, and a blue LED lamp. Of course, the first light source portion 31 may be configured by use of, for example, a halogen lamp or a xenon lamp.

Under control by the light source control unit 34, the second light source portion 32 supplies illumination light that is first narrow band light having a predetermined wavelength band, to the light guide 4 by emitting the first narrow band light. The wavelength band of this first narrow band light is 530 nm to 550 nm (with a central wavelength of 540 nm). The second light source portion 32 is configured by use of, for example, a green LED lamp, a collimator lens, a transmission filter that transmits therethrough light of 530 nm to 550 nm, and a driver.

Under control by the light source control unit 34, the third light source portion 33 supplies illumination light that is second narrow band light having a wavelength band different from that of the first narrow band light, to the light guide 4 by emitting the second narrow band light. The wavelength band of this second narrow band light is 400 nm to 430 nm (with a central wavelength of 515 nm). The third light source portion 33 is implemented by use of, for example, a collimator lens, a semiconductor laser, such as a violet laser diode (LD), and a driver.

The light source control unit 34 is implemented by use of a processor that is a processing device having hardware, such as an FPGA or a CPU, and a memory that is a transitory storage area used by the processor. On the basis of control data input from the control device 9, the light source control unit 34 controls the emission timing and emission time period of each of the first light source portion 31, the second light source portion 32, and the third light source portion 33.

Figure 3:
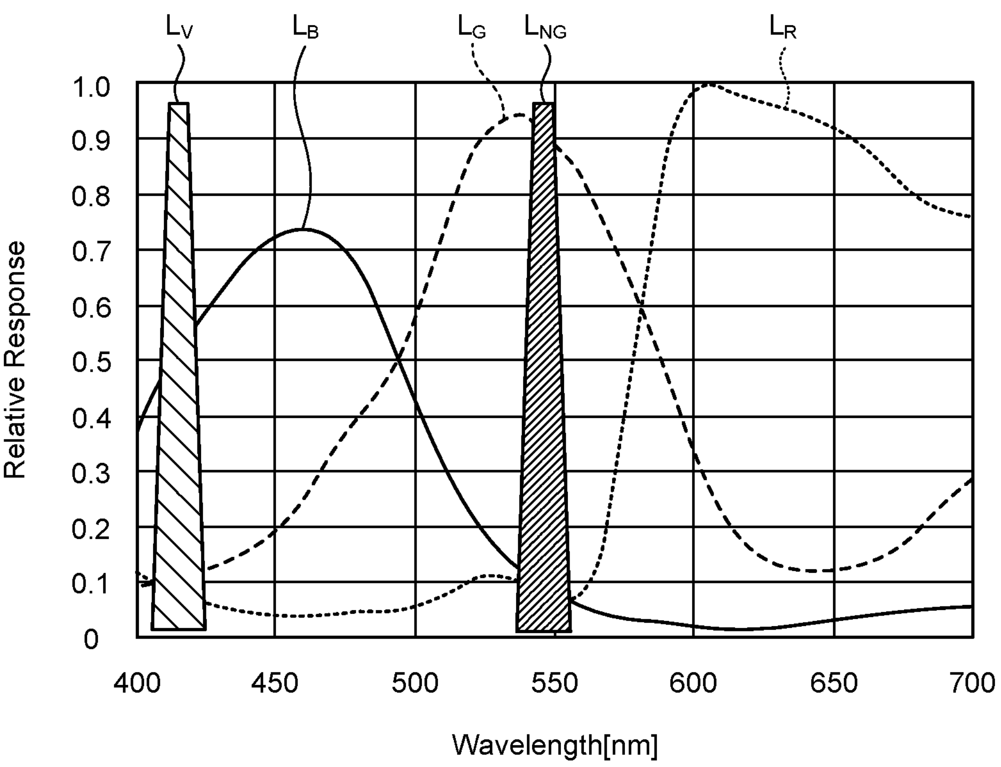
FIG. 3 is a diagram schematically illustrating wavelength characteristics of light emitted by a second light source portion and a third light source portion, according to the first embodiment.

The following is a description of wavelength characteristics of light emitted by each of the second light source portion 32 and the third light source portion 33. FIG. 3 is a diagram schematically illustrating the wavelength characteristics of the light emitted by each of the second light source portion 32 and the third light source portion 33. In FIG. 3, the horizontal axis represents wavelength in nanometers (nm), and the vertical axis represents the wavelength characteristics. In FIG. 3, a polygonal line $L_{NG}$ represents wavelength characteristics of the first narrow band light emitted by the second light source portion 32 and a polygonal line $L_V$ represents wavelength characteristics of the second narrow band light emitted by the third light source portion 33. Furthermore, in FIG. 3, a curve $L_B$ represents a blue wavelength band, a curve $L_G$ represents a green wavelength band, and a curve $L_R$ represents a red wavelength band.

As represented by the polygonal line $L_{NG}$ in FIG. 3, the second light source portion 32 emits the first narrow band light having the central wavelength (peak wavelength) of 540 nm and the wavelength band of 530 nm to 550 nm. The third light source portion 33 emits the second narrow band light having the central wavelength (peak wavelength) of 415 nm and the wavelength band of 400 nm to 430 nm.

As described above, the second light source portion 32 and the third light source portion 33 respectively emit the first narrow band light and second narrow band light having wavelength bands different from each other.

Configuration of Endoscope Camera Head

By reference back to FIG. 2, the description of the configuration of the endoscope system 1 will be continued.

A configuration of the endoscope camera head 5 will be described next. The endoscope camera head 5 includes an optical system 51, a drive unit 52, an imaging element 53, a cut filter 54, an A/D converter 55, a P/S converter 56, an imaging recording unit 57, and an imaging control unit 58.

The optical system 51 forms, on a light receiving surface of the imaging element 53, a subject image condensed by the optical system 22 of the insertion portion 2. The focal length and the focal position of the optical system 51 are able to be changed. The optical system 51 is configured by use of plural lenses 511. In the optical system 51, the plural lenses 511 are moved along an optical axis L1 by the drive unit 52, and the focal distance and focal position are thereby changed.

Under control by the imaging control unit 58, the drive unit 52 moves the plural lenses 511 of the optical system 51 along the optical axis L1. The drive unit 52 is configured by use of: a motor, such as a stepping motor, a DC motor, or a voice coil motor; and a transmission mechanism, such as a gear, that transmits rotation of the motor to the optical system 51.

The imaging element 53 is implemented by use of a charge coupled device (CCD) image sensor or a complementary metal oxide semiconductor (CMOS) image sensor, which has plural pixels arranged in a two-dimensional matrix. Under control by the imaging control unit 58, the imaging element 53 receives, via the cut filter 54, a subject image (light rays) formed by the optical system 51, photoelectrically converts the subject image to generate image data (RAW data), and outputs the image data to the A/D converter 55. The imaging element 53 includes a pixel portion 531 and a color filter 532.

Figure 4:
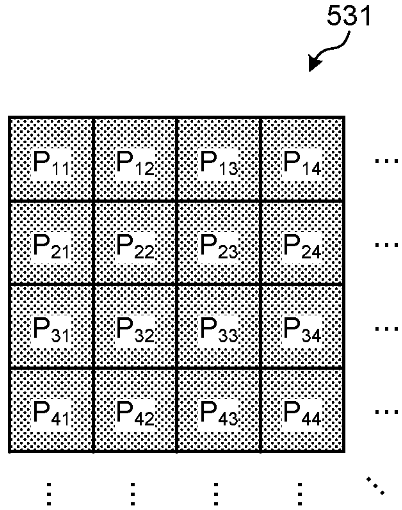
FIG. 4 is a diagram schematically illustrating a configuration of a pixel portion according to the first embodiment.

FIG. 4 is a diagram schematically illustrating a configuration of the pixel portion 531. As illustrated in FIG. 4, the pixel portion 531 has plural pixels $P_{nm}$ (n is an integer equal to or larger than 1 and m is an integer equal to or larger than 1), such as photodiodes that accumulate electric charge corresponding to quantity of light, the plural pixels $P_{nm}$ being arranged in a two-dimensional matrix. Under control by the imaging control unit 58, the pixel portion 531 reads image data that are image signals from some pixels $P_{nm}$ of a read area optionally set as a target to be read from the plural pixels $P_{nm}$ and outputs the image data to the A/D converter 55.

Figure 5:
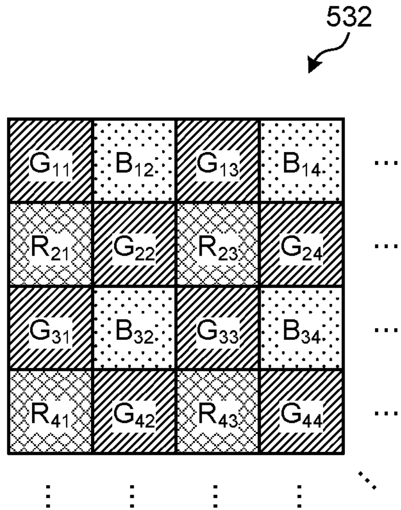
FIG. 5 is a diagram schematically illustrating a configuration of a color filter according to the first embodiment.

FIG. 5 is a diagram schematically illustrating a configuration of the color filter 532. As illustrated in FIG. 5, the color filter 532 has a Bayer arrangement having 2×2 filters as a single unit. The color filter 532 is configured by use of a filter R that transmits therethrough light of the red wavelength band, two filters G that transmit therethrough light of the green wavelength band, and a filter B that transmits therethrough light of the blue wavelength band.

Figure 6:
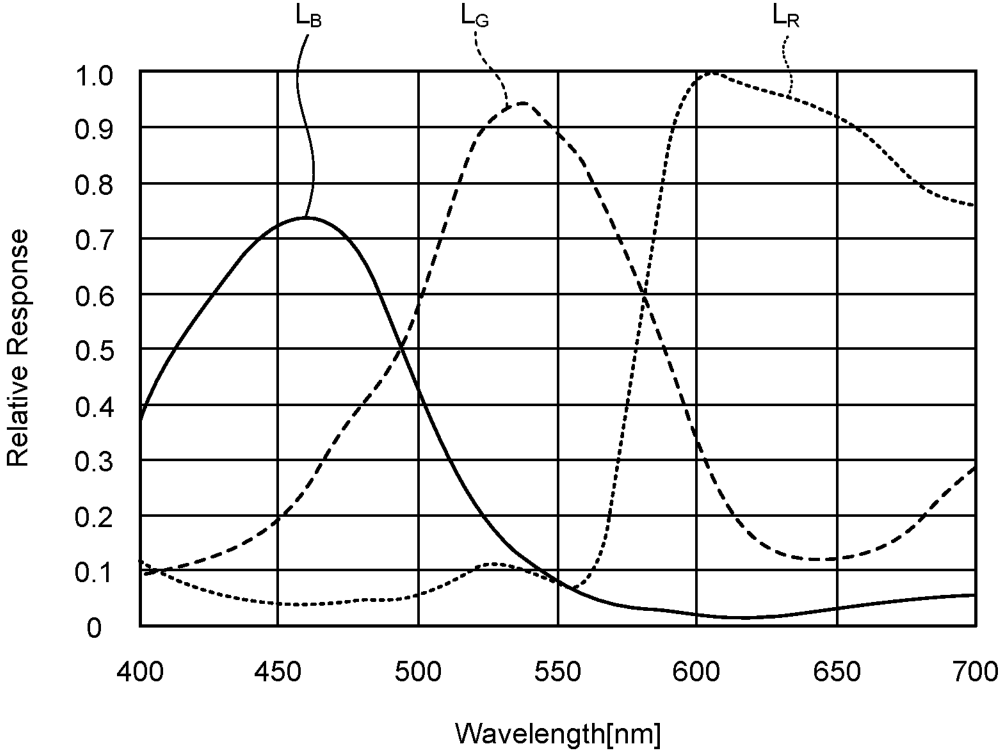
FIG. 6 is a diagram schematically illustrating sensitivity and wavelength bands of filters, according to the first embodiment.

FIG. 6 is a diagram schematically illustrating sensitivity and the wavelength band of each filter. In FIG. 6, the horizontal axis represents wavelength in nanometers (nm) and the vertical axis represents transmission characteristics (sensitivity characteristics). In FIG. 6, a curve $L_B$ represents the transmission characteristics of the filter B, a curve $L_G$ represents transmission characteristics of the filter G, and a curve $L_R$ represents the transmission characteristics of the filter R.

As represented by the curve $L_B$ in FIG. 6, the filter B transmits therethrough light of the blue wavelength band. As represented by the curve $L_G$ in FIG. 6, the filter G transmits therethrough light of the green wavelength band. As represented by the curve $L_R$ in FIG. 6, the filter R transmits therethrough light of the red wavelength band. In the following description, pixels $P_{nm}$ having filters R arranged on light receiving surfaces thereof will be referred to as R pixels, pixels $P_{nm}$ having filters G arranged on light receiving surfaces thereof will be referred to as G pixels, and pixels $P_{nm}$ having filters B arranged on light receiving surfaces thereof will be referred to as B pixels.

In a case where a subject image formed by the optical system 51 is received by the imaging element 53 configured as described above, the imaging element 53 generates, as illustrated in FIG. FIG. 7A to FIG. 7C, color signals (R signals, G signals, and B signals) of the R pixels, G pixels, and B pixels respectively.

By reference back to FIG. 2, the description of the configuration of the endoscope system 1 will be continued.

The cut filter 54 is arranged on the optical axis L1 of the optical system 51 and the imaging element 53. The cut filter 54 is provided on a light receiving surface side (incident surface side) of at least the G pixels provided with the filters G of the color filter 532, the filters G transmitting therethrough light of the green wavelength band. The cut filter 54 shields light of a short wavelength band including the wavelength band of the second narrow band light, and transmits therethrough light that includes the first narrow band light and that is light of a wavelength band longer than the wavelength band of the second narrow band light.

Figure 8:
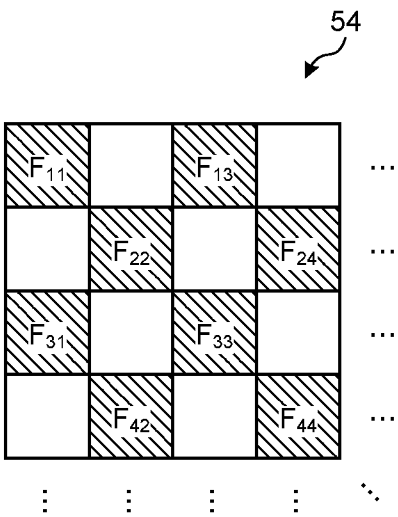
FIG. 8 is a diagram schematically illustrating a configuration of a cut filter according to the first embodiment.

FIG. 8 is a diagram schematically illustrating a configuration of the cut filter 54. As illustrated in FIG. 8, a filter $F_{11}$ included in the cut filter 54 is arranged at a position where a filter $G_{11}$ (see FIG. 5) is arranged and on a light receiving surface side directly above the filter $G_{11}$.

Figure 9:
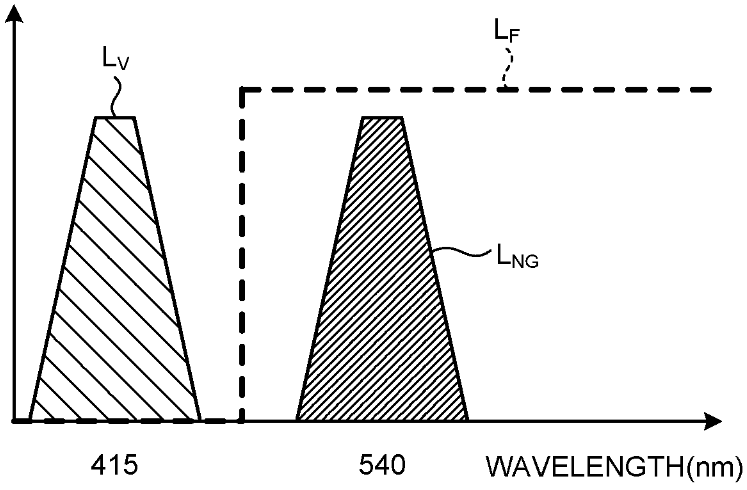
FIG. 9 is a diagram schematically illustrating transmission characteristics of the cut filter according to the first embodiment.

FIG. 9 is a diagram schematically illustrating transmission characteristics of the cut filter 54. In FIG. 9, the horizontal axis represents wavelength in nanometers (nm), and the vertical axis represents the transmission characteristics. Furthermore, in FIG. 9, a polygonal line $L_F$ represents the transmission characteristics of the cut filter 54, the polygonal line $L_{NG}$ represents the wavelength characteristics of the first narrow band light, and the polygonal line $L_V$ represents the wavelength characteristics of the second narrow band light.

As illustrated in FIG. 9, the cut filter 54 shields the second narrow band light and transmits therethrough light of a wavelength band longer than the wavelength band of the second narrow band light. Specifically, the cut filter 54 shields light of a shorter wavelength band including the wavelength band of the second narrow band light and of 400 nm or longer and shorter than 430 nm, and transmits therethrough light of a wavelength band longer than 400 nm to 430 nm including the second narrow band light.

By reference back to FIG. 2, the description of the configuration of the endoscope camera head 5 will be continued.

Under control by the imaging control unit 58, the A/D converter 55 performs A/D conversion processing of analog image data input from the imaging element 53 and outputs the converted image data to the P/S converter 56. The A/D converter 55 is implemented by use of, for example, an A/D conversion circuit.

Under control by the imaging control unit 58, the P/S converter 56 performs parallel/serial conversion of digital image data input from the A/D converter 55, and outputs the image data that has been subjected to the parallel/serial conversion, to the control device 9, via the first transmission cable 6. The P/S converter 56 is implemented by use of, for example, a P/S conversion circuit. In this first embodiment, an E/O converter that converts image data into an optical signal may be provided instead of the P/S converter 56, and the image data may be output through the optical signal to the control device 9, or image data may be transmitted to the control device 9 by wireless communication, such as Wi-Fi (wireless fidelity) (registered trademark), for example.

The imaging recording unit 57 records therein various kinds of information related to the endoscope camera head 5 (for example, pixel information on the imaging element 53 and characteristics of the cut filter 54). Furthermore, the imaging recording unit 57 records therein various kinds of setting data and control parameters transmitted from the control device 9 via the first transmission cable 6. The imaging recording unit 57 is configured by use of a non-volatile memory or a volatile memory.

On the basis of setting data received from the control device 9 via the first transmission cable 6, the imaging control unit 58 controls operation of each of the drive unit 52, the imaging element 53, the A/D converter 55, and the P/S converter 56. The imaging control unit 58 is implemented by use of a timing generator (TG), a processor that is a processing device having hardware, such as a CPU, and a memory that is a transitory storage area used by the processor.

Configuration of Control Device

A configuration of the control device 9 will be described next.

The control device 9 includes an S/P converter 91, an image processing unit 92, an input unit 93, a recording unit 94, and a control unit 95.

Under control by the control unit 95, the S/P converter 91 performs serial/parallel conversion of image data received from the endoscope camera head 5 via the first transmission cable 6, and outputs the converted image data to the image processing unit 92. In a case where the endoscope camera head 5 outputs the image data as an optical signal, an 0/E converter that converts the optical signal into an electric signal may be provided instead of the S/P converter 91. In a case where the endoscope camera head 5 transmits the image data by wireless communication, a communication module capable of receiving a wireless signal may be provided instead of the S/P converter 91.

Under control by the control unit 95, the image processing unit 92 performs predetermined image processing of image data in the form of parallel data input from the S/P converter 91 and outputs the processed image data to the display device 7. This predetermined image processing may include any of demosaicing processing, white balance processing, gain adjustment processing, y correction processing, and format conversion processing. The image processing unit 92 is implemented by use of a processor that is a processing device having hardware, such as a GPU or an FPGA, and a memory that is a transitory storage area used by the processor.

The input unit 93 receives input of various operations related to the endoscope system 1 and outputs the received operations to the control unit 95. The input unit 93 is configured by use of a mouse, a foot switch, a keyboard, a button, a switch, and/or a touch panel, for example.

The recording unit 94 is implemented by use of a volatile memory, a nonvolatile memory, a solid state drive (SSD), a hard disk drive (HDD), and/or a recording medium, such as a memory card. The recording unit 94 records therein data including various parameters needed for operation of the endoscope system 1. The recording unit 94 includes a program recording unit 941 that records therein various programs for operation of the endoscope system 1.

The control unit 95 is implemented by use of a processor that is a processing device having hardware, such as an FPGA or a CPU, and a memory that is a transitory storage area used by the processor. The control unit 95 integrally controls the units included in the endoscope system 1.

Outline of Each Observation Mode

Outlines of observation modes implemented by the endoscope system 1 will be described next. The observation modes will be described hereinafter in the order, a narrow band light observation mode, a heat treatment observation mode, an autofluorescence observation mode, and a normal light observation mode.

Outline of Narrowband Light Observation Mode

The narrow band light observation mode will be described first. FIG. 10 is a diagram schematically illustrating principles of observation in the narrow band light observation mode.

The narrow band light observation mode (narrow band imaging: NBI) corresponds to an observation method of enhancing capillaries of a mucosal surface layer and a mucosal surface structure, of body tissue, by utilization of a property of hemoglobin in blood, the property being of strongly absorbing light near the wavelength of 415 nm. That is, in the narrow band light observation mode, the two types of narrow band light, the first narrow band light (having the wavelength band of 530 nm to 550 nm) and the second narrow band light (having a wavelength band of 390 nm to 445 nm), that are easily absorbed by hemoglobin in blood are emitted to a subject, such as body tissue. Blood vessels in and bloodstream information on a mucosal deep region that are difficult to be visually confirmed with normal light (white light) are thereby able to be highlight-displayed in the narrow band light observation mode.

Specifically, as represented by a graph G1 in FIG. 10, firstly, under control by the control device 9, the light source device 3 causes first narrow band light W1 and second narrow band light W2 to be emitted to body tissue O1 (mucosa) of a subject by causing the second light source portion 32 and the third light source portion 33 to emit light. In this case, part of reflected light and returned light (hereinafter, simply referred to as "reflected light WR1, reflected light WR2, reflected light WG1, reflected light WG2, reflected light WB1, and reflected light WB2") including at least plural components reflected by the body tissue O1 of the subject is shielded by the cut filter 54 and the rest enters the imaging element 53. In the following description, reflected light from the first narrow band light W1 will be referred to as the reflected light WR1, the reflected light WG1, and the reflected light WB1, and reflected light from the second narrow band light W2 will be referred to as the reflected light WR2, the reflected light WG2, and the reflected light WB2. In FIG. 10, thickness of each line represents intensity of a component (quantity of light or signal value).

More specifically, as represented by the polygonal line $L_F$ of a graph G2 in FIG. 10, the cut filter 54 shields the reflected light WG2 to be incident on the G pixels, the reflected light WG2 having a short wavelength band including the wavelength band of the second narrow band light W2.

Furthermore, the cut filter 54 transmits therethrough the reflected light WG1 of a wavelength band including the first narrow band light W1 and longer than the wavelength band of the second narrow band light W2. The reflected light (the reflected light WR1, the reflected light WR2, the reflected light WB1, and the reflected light WB2) resulting from reflection of the first narrow band light W1 and the second narrow band light W2 by the subject enters each of the R pixels and B pixels.

Next, as represented by a graph G3 of transmission characteristics in FIG. 10, the R pixels, G pixels, and B pixels have transmission characteristics (sensitivity characteristics) different from one another. Specifically, the B pixels do not have sensitivity to the reflected light WB1 of the first narrow band light W1 and the output value corresponding to the quantity of the reflected light WB1 received thus becomes minute. On the contrary, the B pixels have sensitivity to the reflected light WB2 of the second narrow band light WW2 and the output value corresponding to the quantity of the reflected light WB1 received thus becomes large.

Thereafter, the image processing unit 92 obtains image data (RAW data) from the imaging element 53 of the endoscope camera head 5, and generates a pseudocolor image (narrow band image) by performing image processing of signal values from the G pixels and B pixels, the signals values being included in the image data obtained. In this case, the signal values from the G pixels include mucosal deep layer information on the subject. Furthermore, the signal values from the B pixels include mucosal surface layer information on the subject. The image processing unit 92 thus generates the pseudocolor image by performing the image processing of the signal values from the G pixels and B pixels, the signal values being included in the image data, the image processing including, for example, gain control processing, pixel interpolation processing, and mucosa enhancement processing, and outputs the pseudocolor image to the display device 7. This pseudocolor image is an image generated by use of only the signal values from the G pixels and the signal values from the B pixels. The image processing unit 92 obtains signal values from the R pixels but deletes these signal values without using them in generating the pseudocolor image.

Accordingly, in the narrow band light observation mode, blood vessels in a mucosal deep region and bloodstream information on the mucosal deep region that are difficult to be visually confirmed with white light (normal light) are able to be highlight-displayed.

Outline of Heat Treatment Observation Mode

Figure 11:
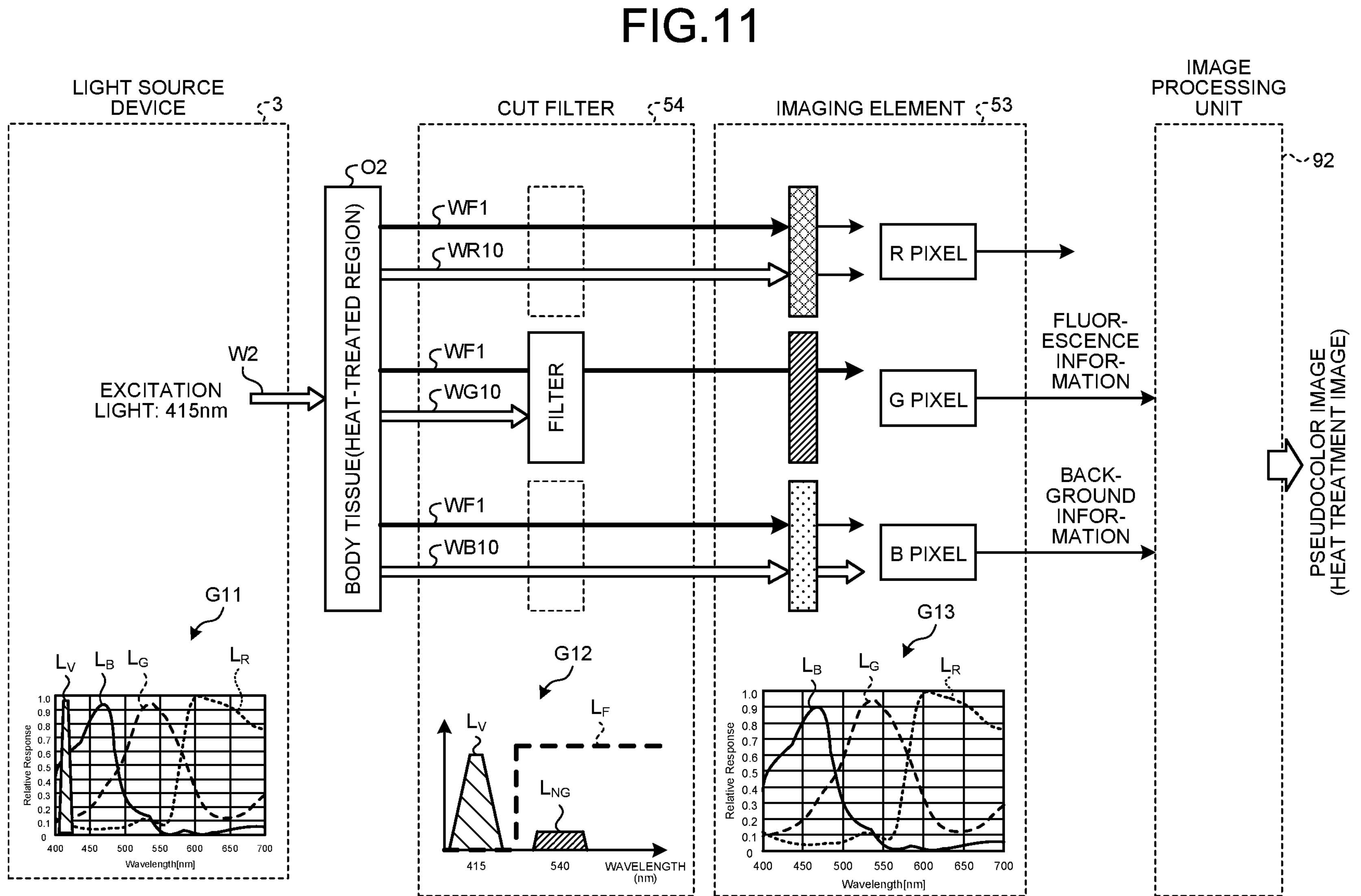
FIG. 11 is a diagram schematically illustrating principles of observation in a heat treatment observation mode according to the first embodiment.

The heat treatment observation mode will be described next. FIG. 11 is a diagram schematically illustrating principles of observation in the heat treatment observation mode.

In recent years, minimally invasive treatments using, for example, endoscopes and laparoscopes have been widely adopted in the medical field. For example, widely adopted ones of the minimally invasive treatments using endoscopes and laparoscopes include endoscopic submucosal dissection (ESD), laparoscopy and endoscopy cooperative surgery (LECS), and non-exposed endoscopic wall-inversion surgery (NEWS).

In these minimally invasive treatments, for example, an operating surgeon, such as a medical doctor, performs pretreatment that is heat treatment or marking treatment by heat treatment, of body tissue, by use of a treatment tool, such as an energy device that may be a high frequency knife or an electrosurgical knife, for marking of a region to be operated. Furthermore, for the actual treatment, the operating surgeon also performs treatment, such as excision and coagulation of the body tissue of the subject by using the energy device, for example.

In reality, the extent of the heat treatment applied to the body tissue by the energy device is checked by the operating surgeon on the basis of, for example, the operating surgeon's visual inspection, sense of touch, and/or guess. Therefore, in a conventional treatment using an energy device, for example, it is difficult for an operating surgeon to check in real time the degree of heat treatment to be applied during the operation in surgery and this check requires great skill and experience. Accordingly, there is a demand from operating surgeons for a technology that enables visualization of a cauterization state of a heat-treated region in heat treatment of body tissue conducted by use of an energy device.

A glycation reaction (the Maillard reaction) occurs when an amino acid and a reducing sugar are heated. End products produced as a result of this Maillard reaction are generally called advanced glycation end products (AGEs). AGEs are known to include a substance having fluorescence.

That is, when body tissue is heat-treated by an energy device, AGEs are produced by the Maillard reaction caused by heating of amino acids and reducing sugars in the body tissue. Fluorescence observation of the AGEs produced by this heating enables visualization of states of the heat treatment. In addition, AGEs are known to emit fluorescence that is more intense than that by autofluorescent substances present in body tissue by nature.

That is, the heat treatment observation mode corresponds to an observation method of visualizing a heat-treated region subjected to heat treatment by utilizing fluorescence of AGEs produced in body tissue by heat treatment by means of, for example, an energy device. Accordingly, in the heat treatment observation mode, blue light near the wavelength of 415 nm for exciting the AGEs is emitted from the light source device 3 to the body tissue. In the heat treatment observation mode, a heat treatment image (a fluorescence image) having, captured therein, fluorescence (for example, green light having a wavelength of 490 nm to 625 nm) generated by the AGEs is thereby able to be observed.

Specifically, as represented by a graph G11 in FIG. 11, firstly, under control by the control device 9, the light source device 3 emits the second narrow band light W2 that is excitation light (with a central wavelength of 415 nm) to body tissue O2 (a heat-treated region) of a subject, the body tissue O2 having been heat-treated by means of, for example, an energy device, by causing the third light source portion 33 to emit light. In this case, as represented by a graph G12 in FIG. 11, reflected light including at least components of the second narrow band light W2 reflected by the body tissue O2 (heat-treated region) and returned light (hereinafter, simply referred to as "the reflected light WR10, the reflected light WG10, and the reflected light WB10") is shielded by the cut filter 54 and some of longer wavelength components enter the imaging element 53. In FIG. 11, thickness of each line represents intensity of a component (quantity of light or signal value).

More specifically, as represented by a graph G12 in FIG. 11, the cut filter 54 shields the reflected light WG10 to be incident on the G pixels, the reflected light WG10 having a short wavelength band including the wavelength band of the second narrow band light W2. Furthermore, as represented by the graph G12 in FIG. 11, the cut filter 54 transmits therethrough fluorescence (WF1) generated by autofluorescence of AGEs in the body tissue O2 (heat-treated region). Therefore, reflected light (the reflected light WR10 and the reflected light WB10) and fluorescence (WF1) enter the R pixels and B pixels. Furthermore, fluorescence (WF1) enters the G pixels. As described above, because the cut filter 54 is arranged on the light receiving surface side (incident surface side) of the G pixels, the fluorescence component is prevented from being buried in the reflected light WG10 of the second narrow band light W2 that is excitation light.

Furthermore, as represented by a polygonal line $L_{NG}$ for fluorescence in the graph G12 in FIG. 11, the G pixels have sensitivity to fluorescence, but because the fluorescence is a minute reaction, the output value becomes small.

Thereafter, the image processing unit 92 obtains image data (RAW data) from the imaging element 53 of the endoscope camera head 5, and generates a pseudocolor image (a heat treatment fluorescence image) by performing image processing of signal values from the G pixels and B pixels, the signal values being included in the image data obtained. In this case, the signal values from the G pixels include fluorescence information generated from the heat-treated region. The signals values from the B pixels include background information on body tissue around the heat-treated region. The image processing unit 92 thus generates the pseudocolor image by performing the image processing of the signal values from the G pixels and B pixels, the signal values being included in the image data, the image processing including, for example, gain control processing, pixel interpolation processing, and mucosa enhancement processing, and outputs the pseudocolor image (heat treatment image) to the display device 7. In this case, the image processing unit 92 performs the gain control processing to make gains for the signal values from the G pixels larger than gains for signal values from the G pixels in normal light observation and make gains for the signal values from the B pixels smaller than gains for signal values from the B pixels in the normal light observation. Furthermore, the image processing unit 92 performs the gain control processing to make the signal values from the G pixels and the signal values from the B pixels the same (1:1).

Accordingly, the heat treatment observation mode facilitates observation of the body tissue O2 (heat-treated region) that is heat-treated by the energy device, for example.

Outline of Autofluorescence Observation Mode

Figure 12:
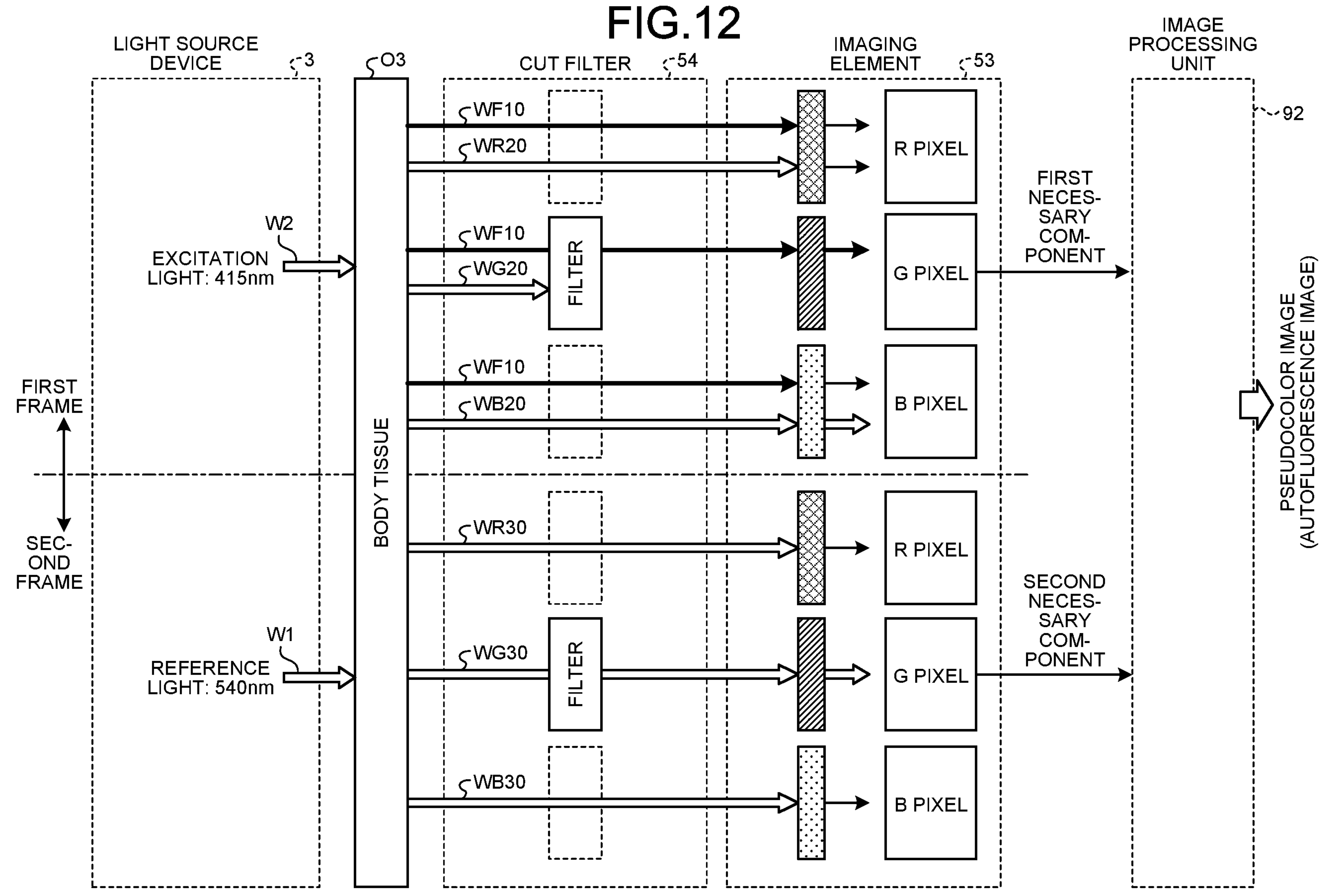
FIG. 12 is a diagram schematically illustrating principles of observation in an autofluorescence observation mode according to the first embodiment.

The autofluorescence observation mode will be described next. FIG. 12 is a diagram schematically illustrating principles of observation in the autofluorescence observation mode.

The autofluorescence observation mode (autofluorescence imaging: AFI) corresponds to an observation method of facilitating discrimination of normal tissue and lesional tissue, such as a tumor, by exciting a fluorescent substance, such as collagen, present in a submucosal layer of body tissue. In the autofluorescence observation mode, excitation light to excite an autofluorescent substance, the excitation light being blue light having a wavelength band near 415 nm, and reference light reflected by a mucosal surface layer of body tissue, the reference light being green light having a wavelength band near 540 nm, are sequentially emitted (alternately emitted). In the autofluorescence observation mode, a fluorescent component emitted by a fluorescent substance present in body tissue and a reflected light component of the reference light returned from normal body tissue are imaged by the imaging element 53, and are displayed as a pseudocolor image that enables discrimination between normal tissue and lesional tissue.

Specifically, as represented by a graph G21 in FIG. 12, firstly, under control by the control device 9, the light source device 3 causes the first narrow band light W1 (with the central wavelength of 540 nm) serving as reference light and the second narrow band light W2 (with the central wavelength of 415 nm) serving as excitation light, to be sequentially emitted (alternately emitted) to body tissue O3 of a subject by causing the second light source portion 32 and the third light source portion 33 to emit light alternately. In this case, part of light including at least reflected light and returned light that include plural components reflected by the subject (hereinafter, simply referred to as the "reflected light WR20, reflected light WG20, and reflected light WB20") is shielded by the cut filter 54 and the rest enters the imaging element 53.

More specifically, as represented by a graph G22 in FIG. 12, the cut filter 54 shields the reflected light WG20 to be incident on the G pixels and having a short wavelength band including the wavelength band of the second narrow band light W2. Specifically, in the autofluorescence observation mode, in a case where the second narrow band light W2 is emitted, fluorescence WF10 (with a central wavelength of 540 nm) enters the G pixels. Furthermore, in the autofluorescence observation mode, in the case where the second narrow band light W2 is emitted, fluorescence WF10 generated from a fluorescent substance in the body tissue O3 and the reflected light WB20 of the second narrow band light W2 enter the B pixels, the reflected light WB20 having been reflected by the body tissue O3, and fluorescence WF10 generated from the fluorescent substance in the body tissue O3 and the reflected light WR20 of the second narrow band light W2 enter the R pixels, the reflected light WR20 having been reflected by the body tissue O3.

Furthermore, in the autofluorescence observation mode, in a case where the first narrow band light W1 is emitted, reflected light WG30 of the first narrow band light W1 (reference light) enters the G pixels, the reflected light WG30 having been reflected by the body tissue O3. In addition, in the autofluorescence observation mode, in the case where the first narrow band light W1 is emitted, reflected light WB30 of the first narrow band light W1 (reference light) enters the B pixels, the reflected light WB30 having been reflected by the body tissue O3, and reflected light WR30 of the first narrow band light W1 (reference light) enters the R pixels, the reflected light WR30 having been reflected by the body tissue O3. In FIG. 12, thickness of each line represents intensity of a component (quantity of light or signal value).

Thereafter, the image processing unit 92 obtains image data (RAW data) from the imaging element 53 of the endoscope camera head 5, and generates a pseudocolor image (autofluorescence image) by performing image processing of signal values from the G pixels, the signal values being included in the image data obtained. In this case, the signal values from the G pixels include: fluorescence information (first necessary component) generated from the fluorescent substance in the body tissue O3 where the second narrow band light W2 enters in the case where the second narrow band light W2 is emitted; and background information (second necessary component) on the reflected reference light including reflected light and returned light that result from reflection of the first narrow band light W1 by the body tissue O3 in the case where the first narrow band light W1 (reference light) is emitted. The quantity of the reflected reference light from a region having a blood vessel or inflammation is smaller than that from a normal tissue region or a region having a hypertrophic superficial mucosa, these regions being of the body tissue O3 irradiated with the first narrow band light W1 (reference light). Therefore, the image processing unit 92 performs enhancement processing so that a region where the fluorescence information (first necessary component) generated from the fluorescent substance in the body tissue O3 is weak and the background information (second necessary component) on the reflected reference light from the body tissue O3 is intense is more enhanced. Specifically, the image processing unit 92 generates a pseudocolor image so that a region presumed to be a tumor is displayed in magenta. For example, the image processing unit 92 assigns the color tone of regional fluorescence information (first necessary component) generated from a fluorescent substance in body tissue to blue and red on a pseudocolor image and assigns the color tone of background information (second necessary component) on reflected reference light from the body tissue to green on the pseudocolor image. A region presumed to be a tumor is thereby represented in magenta and a normal mucosa region or a region having a blood vessel or inflammation is represented in a green color. The image processing unit 92 deletes signal values of the B pixels and R pixels included in the image data without using these signal values.

As illustrated in FIG. 12 described above, in the autofluorescence observation mode, the image processing unit 92 performs gain control processing of making gains for the signal values from the G pixels larger than gains for signal values from the G pixels in the normal light observation.

As described above, in the autofluorescence observation mode, observation of autofluorescence from body tissue enables observation by highlight display of a lesional region (abnormal region), such as a tumor, and a normal region in different color tones.

Outline of Normal Light Observation Mode

The normal light observation mode will be described next. FIG. 13 is a diagram schematically illustrating principles of observation in the normal light observation mode.

As illustrated in FIG. 13, firstly, under control by the control device 9, the light source device 3 emits white light W3 to body tissue O4 of a subject by causing the first light source portion 31 to emit light. In this case, part of reflected light and returned light that are reflected by the body tissue O4 (hereinafter, simply referred to as the "reflected light WR40, reflected light WG40, and reflected light WB40") is shielded by the cut filter 54 and the rest enters the imaging element 53. Specifically, as illustrated in FIG. 13, the cut filter 54 shields the reflected light WG40 to be incident on the G pixels and having a short wavelength band including the wavelength band of the second narrow band light W2. Therefore, as illustrated in FIG. 13, a blue wavelength band light component incident on the G-pixels is less than that in a state without the cut filter 54 arranged in the system.

Next, the image processing unit 92 obtains image data (RAW data) from the imaging element 53 of the endoscope camera head 5, and generates a white light image by performing image processing of signal values from the R pixels, G pixels, and B pixels, the signal values being included in the image data obtained. In this case, because the blue component included in the image data is smaller than that in conventional white light observation, the image processing unit 92 performs white balance adjustment processing of adjusting white balance to make the ratio of the red component, green component, and blue component constant.

As described above, in the normal light observation mode, even in a case where the cut filter 54 is arranged on the light receiving surface side of the G pixels, a natural white image is able to be observed.

Processing by Endoscope System

Processing executed by the endoscope system 1 will be described next. FIG. 14 is a flowchart illustrating an outline of the processing executed by the endoscope system 1. The image processing unit 92 performs various kinds of image processing for developing image data, but for simplification, only characteristic image processing in each observation mode will be described hereinafter.

As illustrated in FIG. 14, firstly, the control unit 95 determines whether or not the endoscope system 1 has been set in the narrow band light observation mode (Step S1). In a case where the control unit 95 determines that the endoscope system 1 has been set in the narrow band light observation mode (Step S1: Yes), the endoscope system 1 proceeds to Step S2 described later. On the contrary, in a case where the control unit 95 determines that the endoscope system 1 has not been set in the narrow band light observation mode (Step S1: No), the endoscope system 1 proceeds to Step S4 described later.

At Step S2, the endoscope system 1 executes narrow band light observation mode processing. After Step S2, the endoscope system 1 proceeds to Step S3 described later.

Narrowband Light Observation Mode Processing

Figure 15:
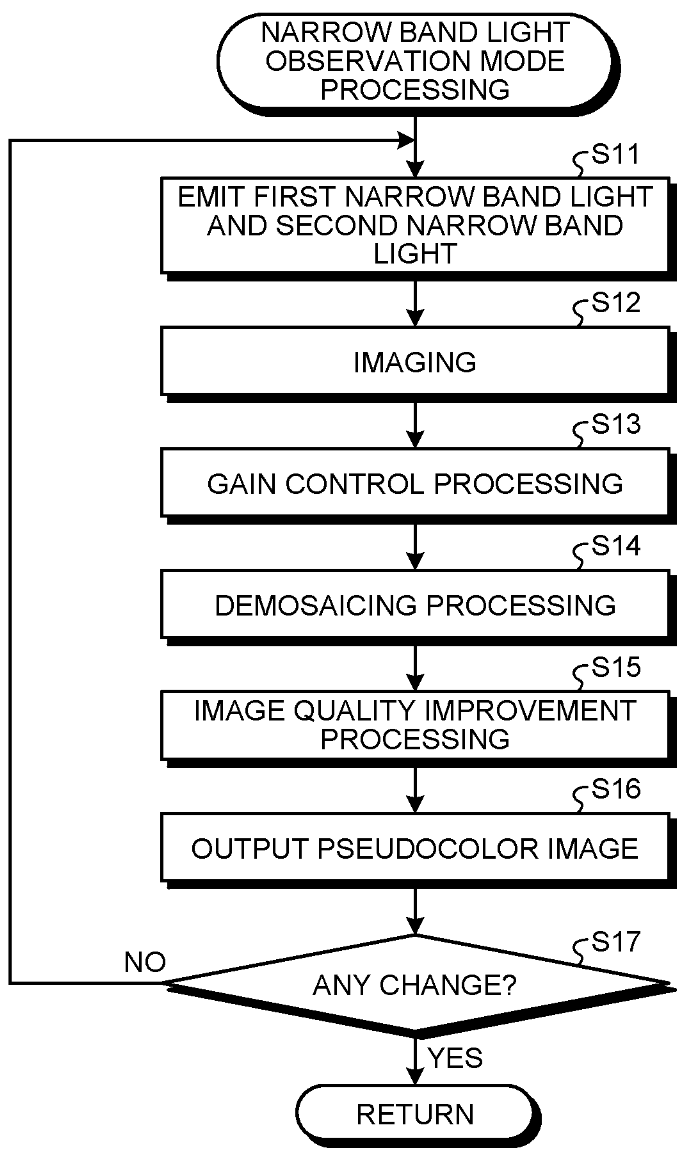
FIG. 15 is a flowchart illustrating an outline of narrow band light observation mode processing in FIG. 14.

FIG. 15 is a flowchart illustrating an outline of the narrow band light observation mode processing at Step S2 in FIG. 14 described above.

As illustrated in FIG. 15, the control unit 95 controls the light source control unit 34 to cause each of the second light source portion 32 and the third light source portion 33 to emit light, and thereby causes the first narrow band light and the second narrow band light to be emitted to a subject (Step S11).

Subsequently, by controlling the imaging control unit 58, the control unit 95 causes the imaging element 53 to capture a subject image condensed by the optical system 22 and optical system 51 and transmitted through the cut filter 54 (Step S12).

Thereafter, the control unit 95 causes the image processing unit 92 to execute gain control processing of image data input via the A/D converter 55, the P/S converter 56, and the S/P converter 91 (Step S13).

Subsequently, the control unit 95 causes the image processing unit 92 to execute demosaicing processing of the image data that have been subjected to the gain control processing (Step S14) and causes the image processing unit 92 to execute image quality improvement processing of the image data that have been subjected to the demosaicing processing and to generate a pseudocolor image (Step S15).

Thereafter, the control unit 95 causes the image processing unit 92 to output the pseudocolor image to the display device 7 (Step S16). An operating surgeon, such as a medical doctor, is thereby able to conduct observation of the subject while looking at the narrow band light image.

Subsequently, the control unit 95 determines whether or not a switching signal to change the observation mode of the endoscope system 1 has been input from the input unit 93 (Step S17). In a case where the control unit 95 determines that the switching signal to change the observation mode of the endoscope system 1 has been input from the input unit 93 (Step S17: Yes), the endoscope system 1 returns to the main routine in FIG. 14. On the contrary, in a case where the control unit 95 determines that the switching signal to change the observation mode of the endoscope system 1 has not been input from the input unit 93 (Step S17: No), the endoscope system 1 returns to Step S11 described above.

By reference back to FIG. 14, description of the processing from Step S3 will be continued.

At Step S3, the control unit 95 determines whether or not an instruction signal to instruct the system to end the observation of the subject has been input from the input unit 93. In a case where the control unit 95 determines that the instruction signal to instruct the system to end the observation of the subject has been input from the input unit 93 (Step S3: Yes), the endoscope system 1 ends the processing. On the contrary, in a case where the control unit 95 determines that the instruction signal to instruct the system to end the observation of the subject has not been input from the input unit 93 (Step S3: No), the endoscope system 1 returns to Step S1 described above.

At Step S4, the control unit 95 determines whether or not the endoscope system 1 has been set in the heat treatment observation mode. In a case where the control unit 95 determines that the endoscope system 1 has been set in the heat treatment observation mode (Step S4: Yes), the endoscope system 1 proceeds to Step S5 described later. On the contrary, in a case where the control unit 95 determines that the endoscope system 1 has not been set in the heat treatment observation mode (Step S4: No), the endoscope system 1 proceeds to Step S6 described later.

At Step S5, the endoscope system 1 executes heat treatment observation mode processing. After Step S5, the endoscope system 1 proceeds to Step S3.

Heat Treatment Observation Mode Processing

Figure 16:
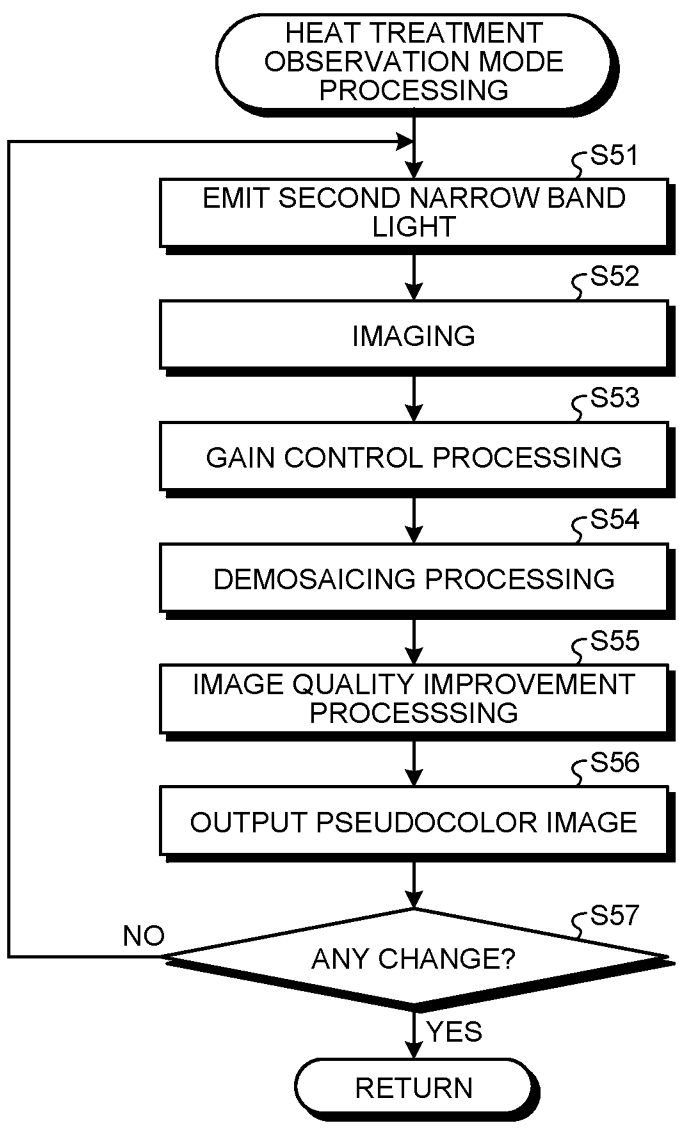
FIG. 16 is a flowchart illustrating an outline of heat treatment observation mode processing in FIG. 14.

FIG. 16 is a flowchart illustrating an outline of the heat treatment observation mode processing at Step S5 in FIG. 14 described above.

As illustrated in FIG. 16, by controlling the light source control unit 34, the control unit 95 causes the third light source portion 33 to emit light to thereby cause the second narrow band light to be emitted to a subject (Step S51).

Subsequently, by controlling the imaging control unit 58, the control unit 95 causes the imaging element 53 to capture a subject image condensed by the optical system 22 and optical system 51 and transmitted through the cut filter 54 (Step S52).

Thereafter, the control unit 95 causes the image processing unit 92 to execute gain control processing of image data input via the A/D converter 55, the P/S converter 56, and the S/P converter 91 (Step S53). In this case, the image processing unit 92 performs the gain control processing of making gains for signal values from the G pixels larger than gains for signal values from the G pixels in normal light observation and make gains corresponding to signal values from the B pixels smaller than gains for signal values from the B pixels in the normal light observation, the signal values being included in the image data. Furthermore, the image processing unit 92 performs the gain control processing to make the signal values from the G pixels and the signal values from the B pixels the same (1:1).

Subsequently, the control unit 95 causes the image processing unit 92 to execute demosaicing processing of the image data that have been subjected to the gain control processing (Step S54) and causes the image processing unit 92 to execute image quality improvement processing of the image data that have been subjected to the demosaicing processing and to generate a pseudocolor image (heat treatment image) (Step S55).

Thereafter, the control unit 95 causes the image processing unit 92 to output the pseudocolor image to the display device 7 (Step S56). An operating surgeon, such as a medical doctor, is thereby able to conduct observation of the subject while looking at the heat treatment image.

Subsequently, the control unit 95 determines whether or not a switching signal to change the observation mode of the endoscope system 1 has been input from the input unit 93 (Step S57). In a case where the control unit 95 determines that the switching signal to change the observation mode of the endoscope system 1 has been input from the input unit 93 (Step S57: Yes), the endoscope system 1 returns to the main routine in FIG. 14. On the contrary, in a case where the control unit 95 determines that the switching signal to change the observation mode of the endoscope system 1 has not been input from the input unit 93 (Step S57: No), the endoscope system 1 returns to Step S51 described above.

By reference back to FIG. 14, description of the processing from Step S6 will be continued.

At Step S6, the control unit 95 determines whether or not the endoscope system 1 has been set in the autofluorescence observation mode. In a case where the control unit 95 determines that the endoscope system 1 has been sent in the autofluorescence observation mode (Step S6: Yes), the endoscope system 1 proceeds to Step S7 described later. On the contrary, in a case where the control unit 95 determines that the endoscope system 1 has not been set in the autofluorescence observation mode (Step S6: No), the endoscope system 1 proceeds to Step S8 described later.

At Step S7, the endoscope system 1 executes autofluorescence observation mode processing. After Step S7, the endoscope system 1 proceeds to Step S3.

Autofluorescence Observation Mode Processing

Figure 17:
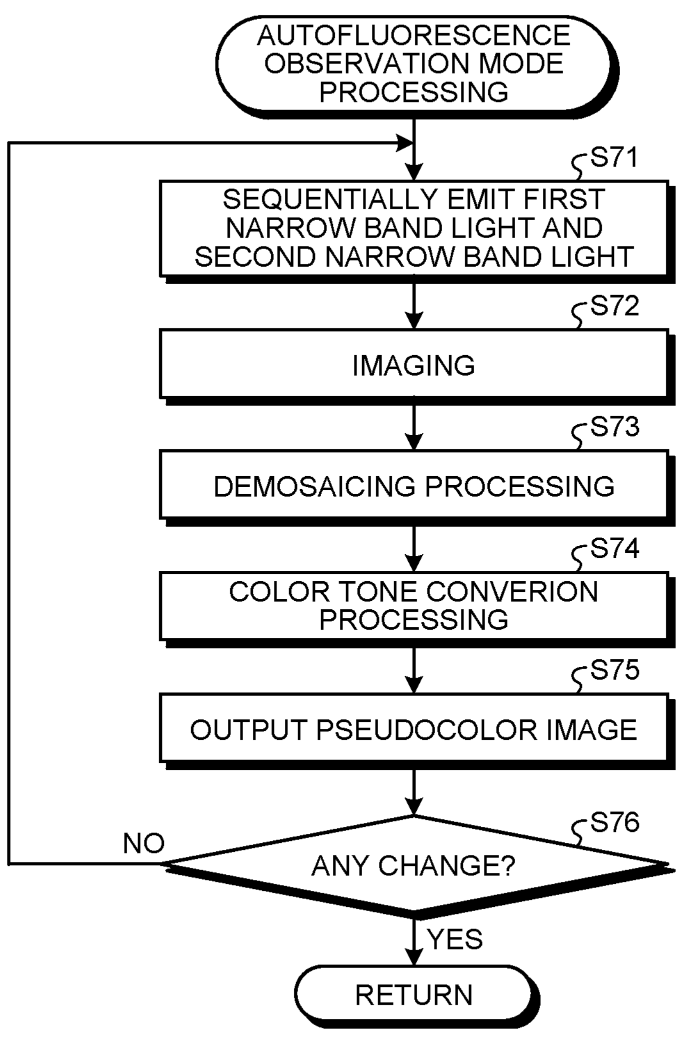
FIG. 17 is a flowchart illustrating an outline of autofluorescence observation mode processing in FIG. 14.

FIG. 17 is a flowchart illustrating an outline of the autofluorescence observation mode processing at Step S7 in FIG. 14 described above.

As illustrated in FIG. 17, the control unit 95 controls the light source control unit 34 to cause each of the second light source portion 32 and the third light source portion 33 to emit light, and thereby causes the first narrow band light and the second narrow band light to be sequentially emitted (alternately emitted) to a subject (Step S71).

Subsequently, by controlling the imaging control unit 58, the control unit 95 causes the imaging element 53 to capture a subject image condensed by the optical system 22 and optical system 51 and transmitted through the cut filter 54 (Step S72).

Thereafter, the control unit 95 causes the image processing unit 92 to execute demosaicing processing of image data input via the A/D converter 55, the P/S converter 56, and the S/P converter 91 (Step S73).

Subsequently, the control unit 95 causes the image processing unit 92 to execute color tone conversion processing of the image data that have been subjected to the demosaicing processing and to generate a pseudocolor image (Step S74). In this case, signal values from the G pixels include: fluorescence information (first necessary component) generated from a fluorescent substance in body tissue where the second narrow band light W2 enters in the case where the second narrow band light W2 is emitted; and background information (second necessary component) on reflected reference light including reflected light and returned light that result from reflection of the first narrow band light W1 by the body tissue in the case where the first narrow band light W1 (reference light) is emitted. The quantity of reflected reference light from a region having a blood vessel or inflammation is smaller than that from a normal tissue region or a region having a hypertrophic superficial mucosa, the regions being of the body tissue irradiated with the first narrow band light W1 (reference light). Therefore, the image processing unit 92 performs enhancement processing so that a region where the fluorescence information (first necessary component) generated by the fluorescent substance in the body tissue is weak and the background information (second necessary component) on the reflected reference light from the body tissue is intense is more enhanced. Specifically, the image processing unit 92 generates a pseudocolor image so that a region presumed to be a tumor is displayed in magenta. For example, the image processing unit 92 assigns the color tone of regional fluorescence information (first necessary component) generated from a fluorescent substance in body tissue to blue and red on a pseudocolor image and assigns the color tone of background information (second necessary component) on reflected reference light from the body tissue to green on the pseudocolor image. A region presumed to be a tumor is represented in magenta, and a normal mucosa region or a region having a blood vessel or inflammation is represented in a green color. The image processing unit 92 deletes signal values from the B pixels and R pixels, the signal values being included in the image data, without using these signal values.

Thereafter, the control unit 95 causes the image processing unit 92 to output the pseudocolor image to the display device 7 (Step S75). An operating surgeon, such as a medical doctor, is thereby able to conduct observation of an abnormal site including, for example, a tumor, in the subject while looking at the autofluorescence image.

Subsequently, the control unit 95 determines whether or not a switching signal to change the observation mode of the endoscope system 1 has been input from the input unit 93 (Step S76). In a case where the control unit 95 determines that the switching signal to change the observation mode of the endoscope system 1 has been input from the input unit 93 (Step S76: Yes), the endoscope system 1 returns to the main routine in FIG. 14. On the contrary, in a case where the control unit 95 determines that the switching signal to change the observation mode of the endoscope system 1 has not been input by the input unit 93 (Step S76: No), the endoscope system 1 returns to Step S71 described above.

By reference back to FIG. 14, description of the processing from Step S8 will be continued.

At Step S8, the control unit 95 determines whether or not the endoscope system 1 has been set in the normal light observation mode. In a case where the control unit 95 determines that the endoscope system 1 has been set in the normal light observation mode (Step S8: Yes), the endoscope system 1 proceeds to Step S9 described later. On the contrary, in a case where the control unit 95 determines that the endoscope system 1 has not been set in the normal light observation mode (Step S8: No), the endoscope system 1 proceeds to Step S3.

Normal Light Observation Mode Processing

Figure 18:
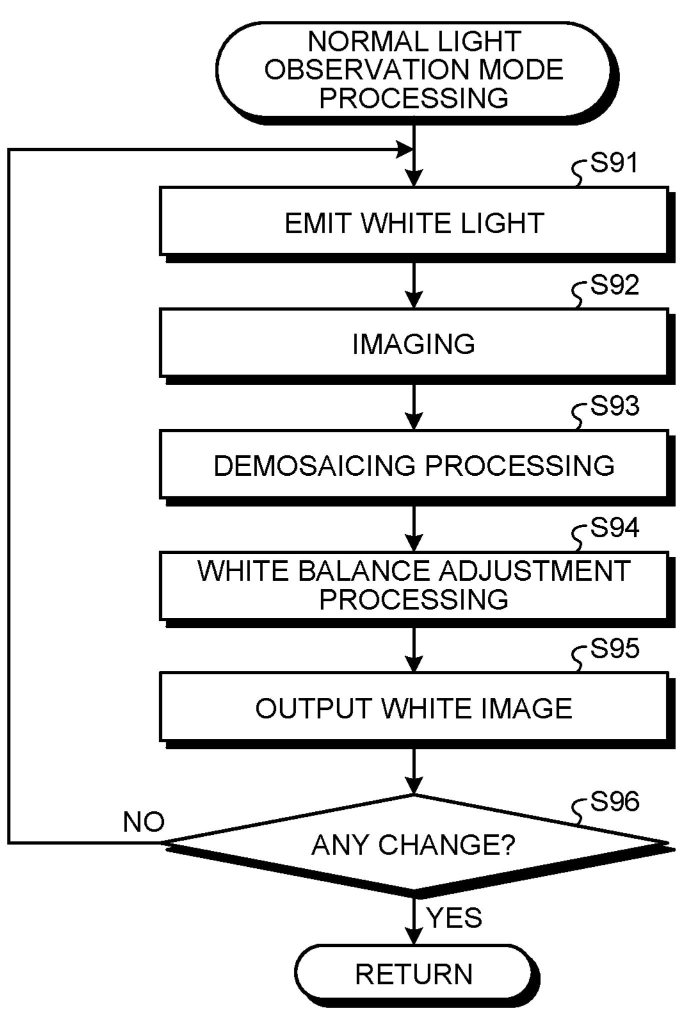
FIG. 18 is a flowchart illustrating an outline of normal light observation mode processing in FIG. 14.

FIG. 18 is a flowchart illustrating an outline of normal light observation mode processing at Step S9 in FIG. 14 described above.

As illustrated in FIG. 18, the control unit 95 causes the first light source portion 31 to emit light by controlling the light source control unit 34 and thereby causes white light to be emitted to a subject (Step S91).

Subsequently, by controlling the imaging control unit 58, the control unit 95 causes the imaging element 53 to capture a subject image condensed by the optical system 22 and optical system 51 and transmitted through the cut filter 54 (Step S92).

Thereafter, the control unit 95 causes the image processing unit 92 to execute demosaicing processing of image data input via the A/D converter 55, the P/S converter 56, and the S/P converter 91 (Step S93).

Subsequently, the control unit 95 causes the image processing unit 92 to execute white balance adjustment processing of the image data that have been subjected to the demosaicing processing and to generate a white image (Step S94). Specifically, because the blue component included in the image data is less than that in conventional white light observation, the image processing unit 92 performs white balance adjustment processing of adjusting white balance to make the ratio of the red component, green component, and blue component constant and generates the white image.

Thereafter, the control unit 95 causes the image processing unit 92 to output the white image to the display device 7 (Step S95). An operating surgeon, such as a medical doctor, is thereby able to conduct observation of the subject while looking at the white image.

Subsequently, the control unit 95 determines whether or not a switching signal to change the observation mode of the endoscope system 1 has been input from the input unit 93 (Step S96). In a case where the control unit 95 determines that the switching signal to change the observation mode of the endoscope system 1 has been input from the input unit 93 (Step S96: Yes), the endoscope system 1 returns to the main routine in FIG. 14. On the contrary, in a case where the control unit 95 determines that the switching signal to change the observation mode of the endoscope system 1 has not been input from the input unit 93 (Step S96: No), the endoscope system 1 returns to Step S71 described above.

The first embodiment described above enables, by the single imaging element 53, both narrow band light observation and observation of fluorescence generated by heat treatment using an energy device, for example, because the cut filter 54 is provided on the light receiving surface side of the pixels provided with the filters G and the cut filter 54 shields shorter wavelength light including the wavelength band of the second narrow band light and transmits therethrough the first narrow band light.

Furthermore, the first embodiment enables, by means of the single imaging element 53, both narrow band light observation and observation of fluorescence generated by heat treatment using an energy device, for example, because the image processing unit 92 generates a narrow band light image (pseudocolor image) on the basis of blue component signals and green component signals in the narrow band light observation mode, and generates a heat treatment image (pseudocolor image) on the basis of blue component signals and green component signals in the heat treatment observation mode.

Furthermore, according to the first embodiment, in a case where only the second narrow band light is emitted to an advanced glycation end product by the light source device 3, the image processing unit 92 makes gains for blue component signals smaller than gains for green component signals, and fluorescence included in a heat treatment image is thus able to be enhanced relatively to the background Furthermore, the first embodiment enables, by means of the single imaging element 53, all of narrow band light observation, observation of fluorescence generated by heat treatment using an energy device, for example, and normal light observation, because in the normal light observation mode, the image processing unit 92 generates a white image by adjusting the white balance so that the ratio of values of the red component signals, green component signals, and blue component signals included in image data becomes constant.

Second Embodiment

A second embodiment will be described next. An endoscope system according to a second embodiment has the same configuration as the above described endoscope system 1 according to the first embodiment, but executes processing different from that of the endoscope system 1. Specifically, in the first embodiment described above, the observation mode is switched between plural observation modes, but in this second embodiment, two sets of image data having different characteristics are generated by alternate execution of plural observation modes, and recording is conducted through manual switching by an operating surgeon, such as a medical doctor, or recording is conducted by switching between images displayed by a display device when a predetermined condition is met. The processing executed by the endoscope system according to the second embodiment will thus be described hereinafter. The same reference signs will be assigned to components of the second embodiment that are the same as those of the above described endoscope system 1 according to the first embodiment, and detailed description of these components will thus be omitted.

Processing by Endoscope System

Figure 19:
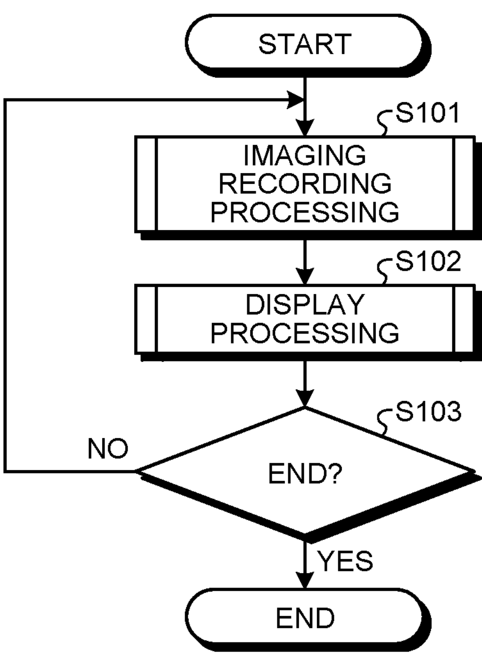
FIG. 19 is a flowchart illustrating an outline of processing executed by an endoscope system according to a second embodiment.

FIG. 19 is a flowchart illustrating an outline of the processing executed by the endoscope system 1 according to the second embodiment. For simplification, a case where the endoscope system 1 performs the normal light observation and heat treatment observation described above will be described with respect to FIG. 19.

As illustrated in FIG. 19, firstly, the endoscope system 1 executes imaging recording processing of irradiating body tissue of a subject with white light or the second narrow band light and imaging and recording returned light, reflected light, and fluorescence from the body tissue (Step S101), and executes display processing of displaying an image based on image data captured (Step S102). Details of the imaging recording processing and display processing will be described later.

Subsequently, the control unit 95 determines whether or not an instruction signal to instruct the system to end the observation of the subject has been input from the input unit 93 (Step S103). In a case where the control unit 95 determines that the instruction signal to instruct the system to end the observation of the subject has been input from the input unit 93 (Step S103: Yes), the endoscope system 1 ends the processing. On the contrary, in a case where the control unit 95 determines that the instruction signal to instruct the system to end the observation of the subject has not been input from the input unit 93 (Step S103: No), the endoscope system 1 returns to Step S101 described above.

Imaging Recording Processing

Figure 20:
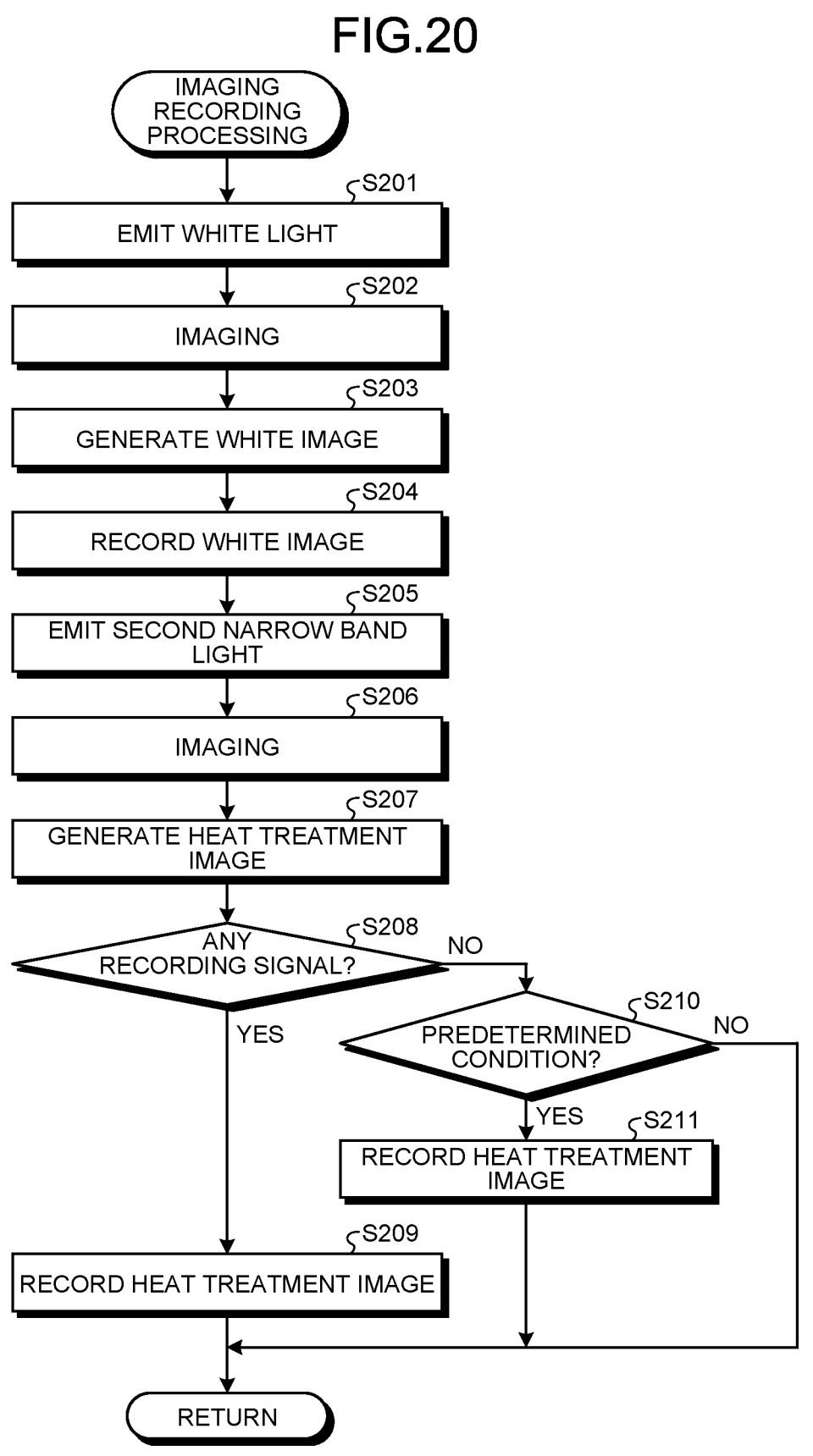

Details of the imaging recording processing at Step S101 in FIG. 19 described above will be described next. FIG. 20 is a flowchart illustrating an outline of the imaging recording processing.

As illustrated in FIG. 20, the control unit 95 causes the first light source portion 31 to emit light by controlling the light source control unit 34 and thereby causes white light to be emitted to the subject (Step S201).

Subsequently, by controlling the imaging control unit 58, the control unit 95 causes the imaging element 53 to capture a subject image condensed by the optical system 22 and optical system 51 and transmitted through the cut filter 54 (Step S202).

Thereafter, the control unit 95 causes the image processing unit 92 to execute predetermined image processing of image data input via the A/D converter 55, the P/S converter 56, and the S/P converter 91 and to generate a white image (Step S203).

Subsequently, the control unit 95 records the white image generated by the image processing unit 92 into the recording unit 94 (Step S204).

Thereafter, the control unit 95 controls the light source control unit 34 to cause the third light source portion 33 to emit light, and thereby causes the second narrow band light to be emitted to the subject (Step S205).

Subsequently, by controlling the imaging control unit 58, the control unit 95 causes the imaging element 53 to capture a subject image condensed by the optical system 22 and optical system 51 and transmitted through the cut filter 54 (Step S206).

Thereafter, the control unit 95 causes the image processing unit 92 to execute predetermined image processing of image data input via the A/D converter 55, the P/S converter 56, and the S/P converter 91 and to generate a heat treatment image (Step S207).

Subsequently, the control unit 95 determines whether or not a recording signal to record the heat treatment image has been input from the input unit 93 (Step S208). Specifically, in a case where an operating surgeon, such as a medical doctor, performs heat treatment of body tissue by means of an energy device, for example, by operating the input unit 93, the control unit 95 determines whether or not a recording signal to record a heat treatment image captured, into the recording unit 94, has been input from the input unit 93. In a case where the control unit 95 determines that the recording signal to record the heat treatment image has been input from the input unit 93 (Step S208: Yes), the endoscope system 1 proceeds to Step S209 described later. On the contrary, in a case where the control unit 95 determines that the recording signal to record the heat treatment image has not been input from the input unit 93 (Step S209: No), the endoscope system 1 proceeds to Step S210 described later.

At Step S209, the control unit 95 records the heat treatment image generated by the image processing unit 92, into the recording unit 94. After Step S209, the endoscope system 1 returns to the main routine in FIG. 19 described above.

At Step S210, the control unit 95 determines whether or not a predetermined condition has been met. Specifically, the control unit 95 determines, on the basis of a driving signal input from, for example, the energy device, whether or not, the energy device has started heat treatment. Furthermore, the control unit 95 determines whether or not the predetermined condition has been met, on the basis of: a state of the body tissue included in the heat treatment image generated by the image processing unit 92, the body tissue having been subjected to the heat treatment; and/or the quantity of fluorescence emitted. For example, in a case where the quantity of fluorescence emitted is equal to or larger than a predetermined threshold, the control unit 95 determines that the predetermined condition has been met. In addition, the control unit 95 determines whether or not the predetermined condition has been met, on the basis of: an area of a fluorescent region of the body tissue subjected to the heat treatment, the fluorescent region being included in the heat treatment image generated by the image processing unit 92. For example, the control unit 95 determines whether or not the area of the fluorescent region included in the heat treatment image is equal to or larger than a predetermined threshold. In a case where the control unit 95 determines that the predetermined condition has been met (Step S210: Yes), the endoscope system 1 proceeds to Step S211 described later. On the contrary, in a case where the control unit 95 determines that the predetermined condition has not been met (Step S210: No), the endoscope system 1 returns to the main routine in FIG. 19 described above.

At Step S211, the control unit 95 records the heat treatment image generated by the image processing unit 92, into the recording unit 94. After Step S211, the endoscope system 1 returns to the main routine in FIG. 19 described above.

Display Processing

Figure 21:
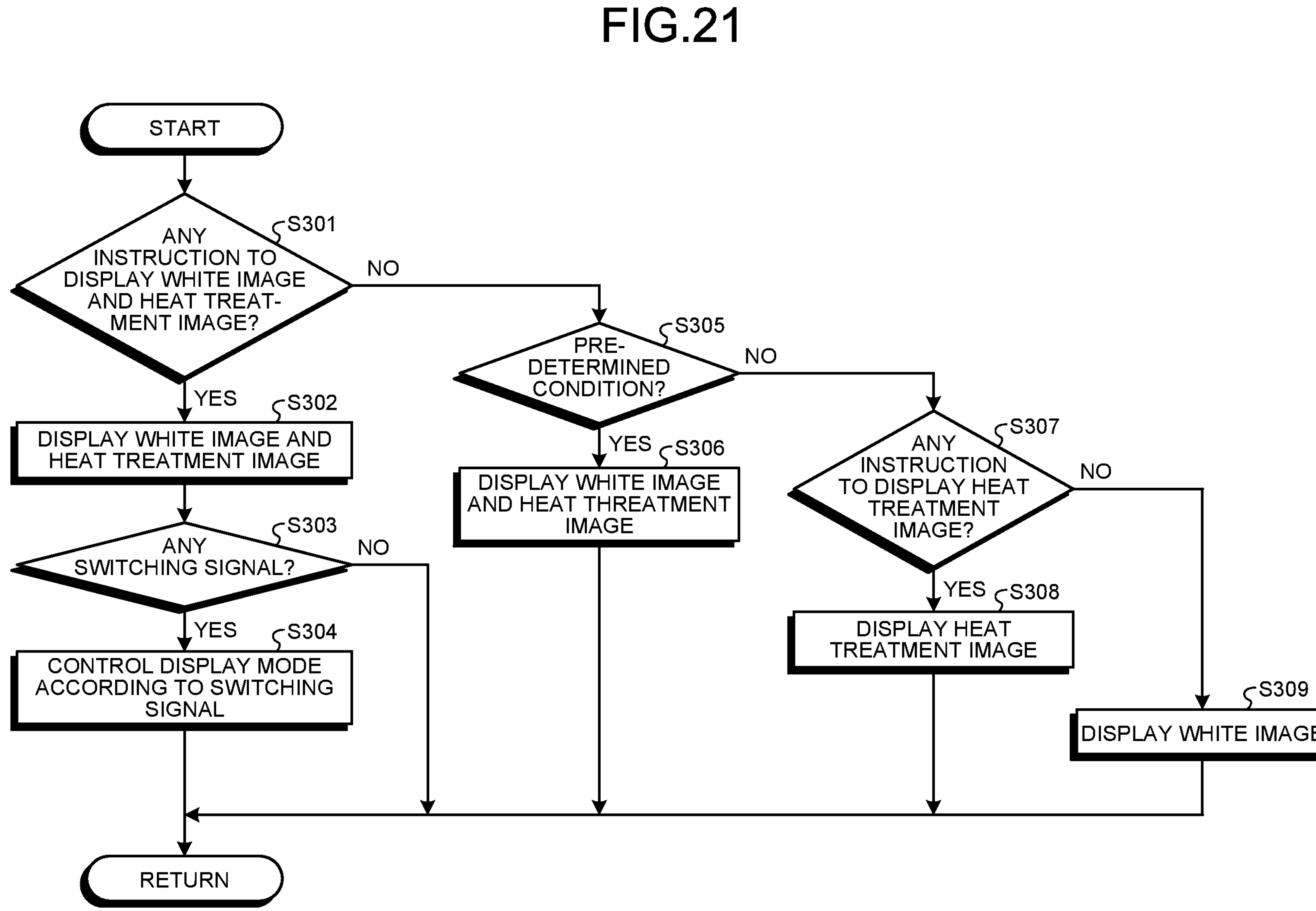
FIG. 21 is a flowchart illustrating an outline of display processing in FIG. 19.

An outline of the display processing at Step S102 in FIG. 19 described above will be described next. FIG. 21 is a flowchart illustrating the outline of the display processing.

As illustrated in FIG. 21, the control unit 95 determines whether or not an instruction signal to instruct display of a white image and a heat treatment image has been input from the input unit 93 (Step S301). In a case where the control unit 95 determines that the instruction signal to instruct the display of the white image and the heat treatment image has been input from the input unit 93 (Step S301: Yes), the endoscope system 1 proceeds to Step S302 described later. On the contrary, in a case where the control unit 95 determines that the instruction signal to instruct the display of the white image and the heat treatment image has not been input from the input unit 93 (Step S301: No), the endoscope system 1 proceeds to Step S305 described later.

Figure 22:
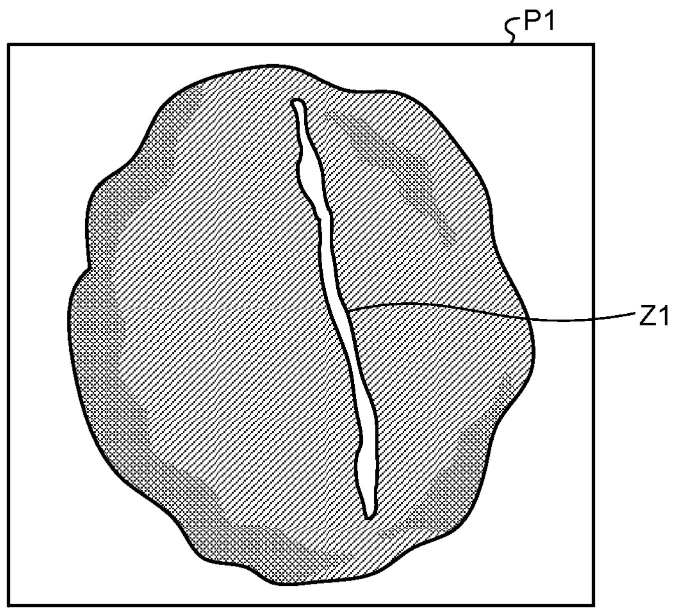
FIG. 22 is a diagram illustrating an example of an image displayed by a display device according to the second embodiment.

At Step S302, the control unit 95 causes the white image and the heat treatment image to be displayed by the display device 7 by causing the image processing unit 92 to output the white image and the heat treatment image. FIG. 22 is a diagram illustrating an example of an image displayed by the display device 7. As illustrated in FIG. 22, the control unit 95 causes the display device 7 to display a combined image P1 that is a combination of a white image and a heat treatment image. In this case, the image processing unit 92 combines the white image and the heat treatment image such that a combination ratio between the white image and the heat treatment image becomes 1:1. Of course, the image processing unit 92 may change, as appropriate, the combination ratio according to an instruction signal input from the input unit 93. Furthermore, the image processing unit 92 may combine only a fluorescent region in the heat treatment image, for example, pixels of the heat treatment image, with the white image, the pixels having signal values equal to or larger than a threshold. An operating surgeon, such as a medical doctor, is thereby able to intuitively know a heat-treated region Z1 including the position of heat treatment by the energy device, for example, by observing a combined image P1 that is a combination of the white image and the heat treatment image. Of course, in the second embodiment, a combined image may be a superimposed image having a heat treatment image superimposed on a white image.

Subsequently, the control unit 95 determines whether or not a switching signal to change the display mode of an image displayed by the display device 7 has been input from the input unit 93 (Step S303). In a case where the control unit 95 determines that the switching signal to change the display mode of the image displayed by the display device 7 has been input from the input unit 93 (Step S303: Yes), the endoscope system 1 proceeds to Step S304 described later. On the contrary, in a case where the control unit 95 determines that the switching signal to change the display mode of the image displayed by the display device 7 has not been input from the input unit 93 (Step S303: No), the endoscope system 1 returns to the main routine in FIG. 19.

At Step S304, the control unit 95 causes a white image and a heat treatment image to be generated and output to the display device 7, the white image and heat treatment image being in a display mode according to the switching signal input from the input unit 93, and thereby controls the display mode of the image displayed by the display device 7. After Step S304, the endoscope system 1 returns to the main routine in FIG. 19.

Figure 23:
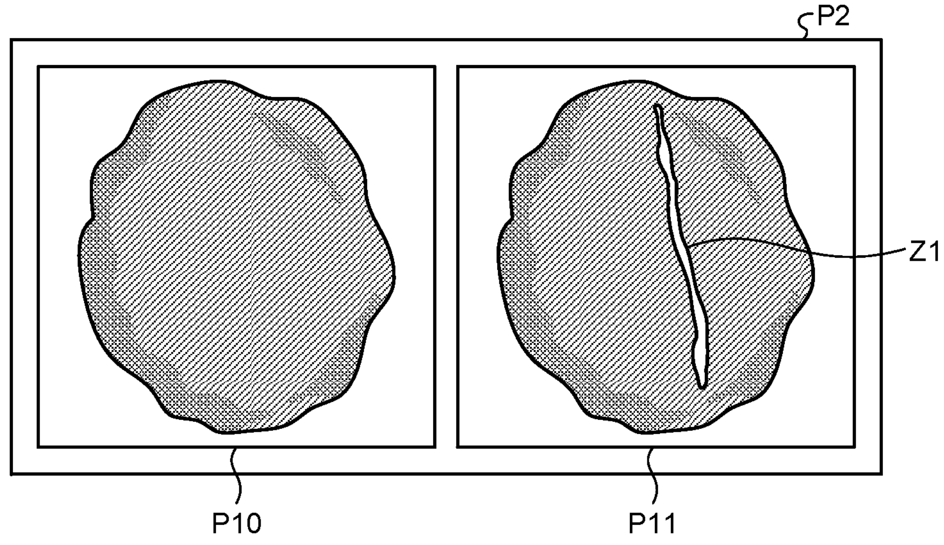
FIG. 23 is a diagram illustrating an example of an image displayed by the display device according to the second embodiment.

FIG. 23 is a diagram illustrating an example of an image displayed by the display device 7. As illustrated in FIG. 23, the control unit 95 causes the image processing unit 92 to generate a display image P2 having a white image P10 and a heat treatment image P11 juxtaposed to each other and to output the display image P2 to the display device 7. An operating surgeon, such as a medical doctor, is thereby able to intuitively know the heat-treated region Z1 including the position of the heat treatment by a treatment tool, such as an energy device, for example, by observing the display image P2 while comparing the white image P10 and the heat treatment image P11 to each other.

Figure 24:
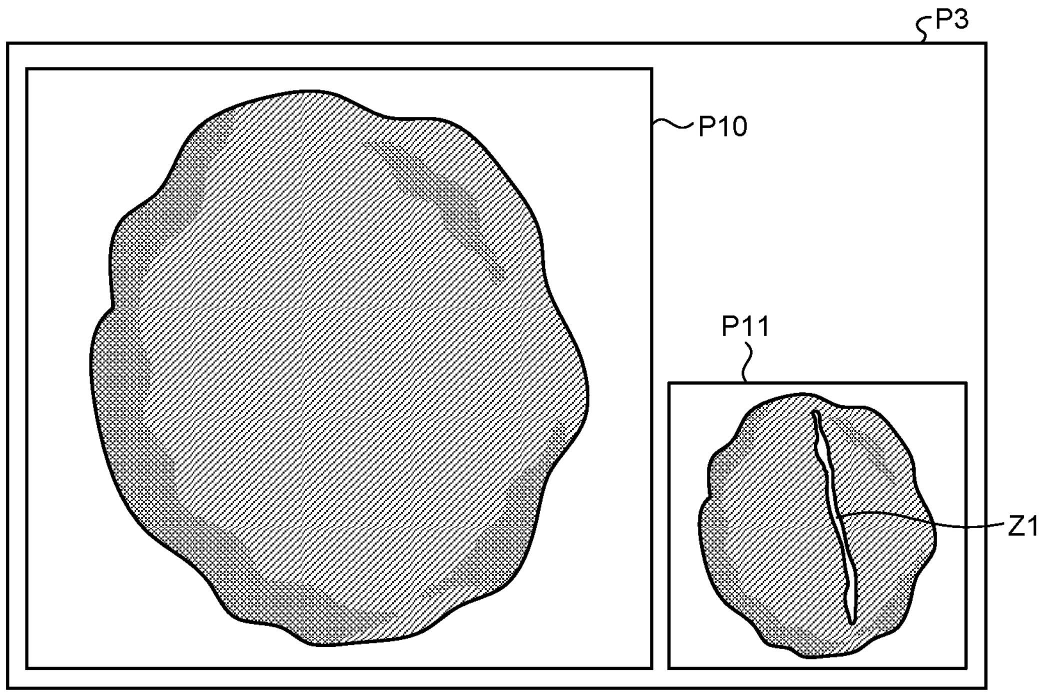
FIG. 24 is a diagram illustrating another example of the image displayed by the display device according to the second embodiment.

FIG. 24 is a diagram illustrating another example of the image displayed by the display device 7. As illustrated in FIG. 24, the control unit 95 causes the image processing unit 92 to generate a display image P3 and to output the display image P3 to the display device 7, the display image P3 having the white image P10 and the heat treatment image P11 juxtaposed to each other. In this display image P3, a display area of the heat treatment image P11 is smaller than a display area of the white image P10. An operating surgeon, such as a medical doctor, is thereby able to intuitively know the heat-treated region Z1 including the position of the heat treatment by the energy device, for example, by observing the display image P3 while comparing the white image P10 and the heat treatment image P11 to each other. The control unit 95 may cause the image processing unit 92 to generate the display image P3 with the display ratio of the heat treatment image P11 and the white image P10 in the display image P3 changed according to an instruction signal from the input unit 93.

Figure 25A:
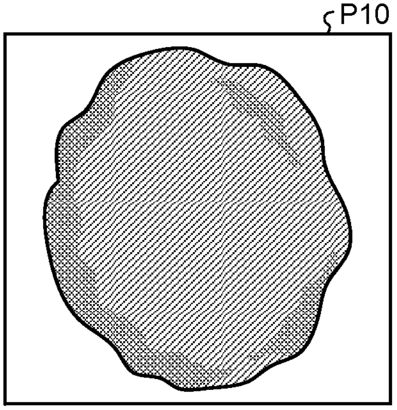
FIG. 25A is a diagram illustrating another example of the image displayed by the display device according to the second embodiment.
Figure 25B:
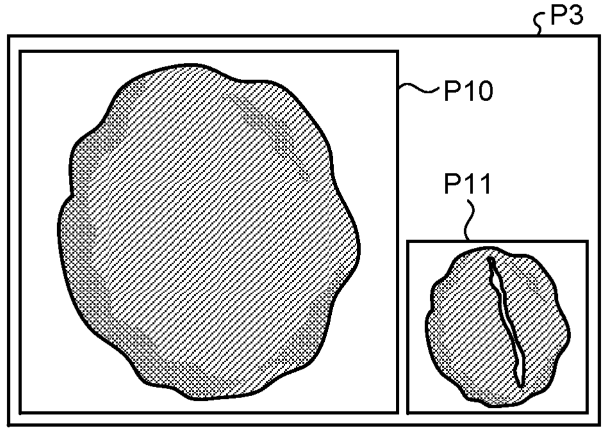
FIG. 25B is a diagram illustrating another example of the image displayed by the display device according to the second embodiment.
Figure 25C:
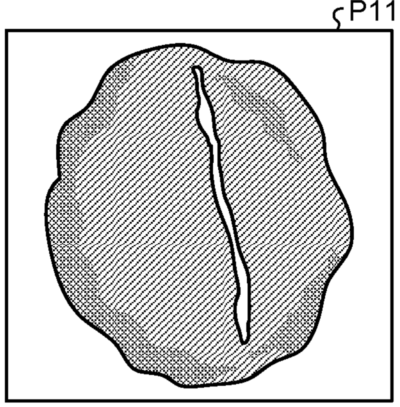
FIG. 25C is a diagram illustrating another example of the image displayed by the display device according to the second embodiment.

FIG. 25A to FIG. 25C are diagrams illustrating other examples of the image displayed by the display device 7. As illustrated in FIG. 25A to FIG. 25C, according to the number of times of input of a switching signal by the input unit 93, the control unit 95 may cause the image processing unit 92 to change the image to be output in the order, the white image P10 (FIG. 25A), the display image P3 (FIG. 25B), and the heat treatment image P11 (FIG. 25C), and to thereby cause the image to be displayed by the display device 7. An operating surgeon, such as a medical doctor, is able to observe a desired image by streamlined operations.

By reference back to FIG. 21, description of the processing from Step S305 will be continued.

At Step S305, the control unit 95 determines whether or not a predetermined condition has been met. Specifically, the control unit 95 determines, on the basis of a driving signal input from, for example, an energy device, whether or not, the energy device has started or ended heat treatment. Furthermore, the control unit 95 determines whether or not the predetermined condition has been met, on the basis of: a state of the body tissue included in the heat treatment image generated by the image processing unit 92, the body tissue having been subjected to the heat treatment; and/or quantity of fluorescence emitted. For example, in a case where the quantity of fluorescence emitted is equal to or larger than a predetermined threshold, the control unit 95 determines that the predetermined condition has been met. Furthermore, the control unit 95 determines whether or not the predetermined condition has been met, on the basis of: an area of a fluorescent region of the body tissue subjected to the heat treatment, the fluorescent region being included in the heat treatment image generated by the image processing unit 92. For example, the control unit 95 determines whether or not the area of the fluorescent region included in the heat treatment image is equal to or larger than a predetermined threshold. In a case where the control unit 95 determines that the predetermined condition has been met (Step S305: Yes), the endoscope system 1 proceeds to Step S306 described later. On the contrary, in a case where the control unit 95 determines that the predetermined condition has not been met (Step S305: No), the endoscope system 1 proceeds to Step S309 described later.

At Step S306, the control unit 95 causes a combined image to be generated and output to the display device 7, the combined image being a combination of a white image and a heat treatment image, and thereby causes the display device 7 to display the combined image. After Step S306, the endoscope system 1 returns to the main routine in FIG. 19.

Figure 26:
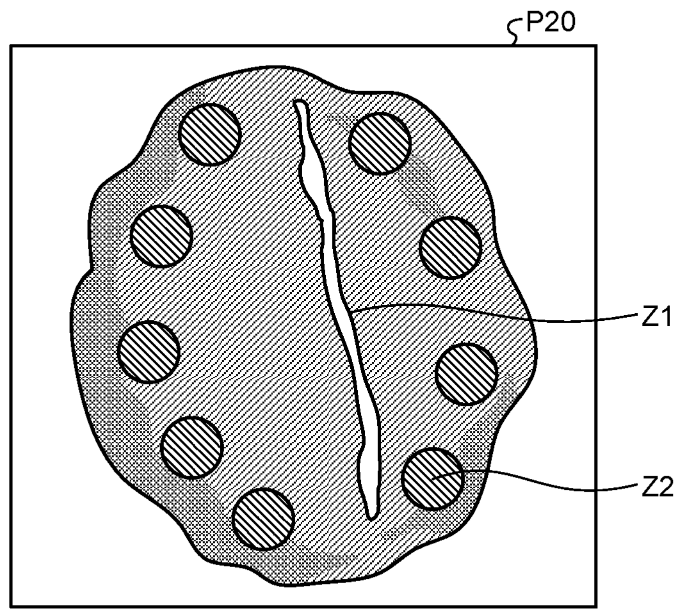
FIG. 26 is a diagram illustrating an example of an image displayed by the display device according to the second embodiment.
Figure 27:
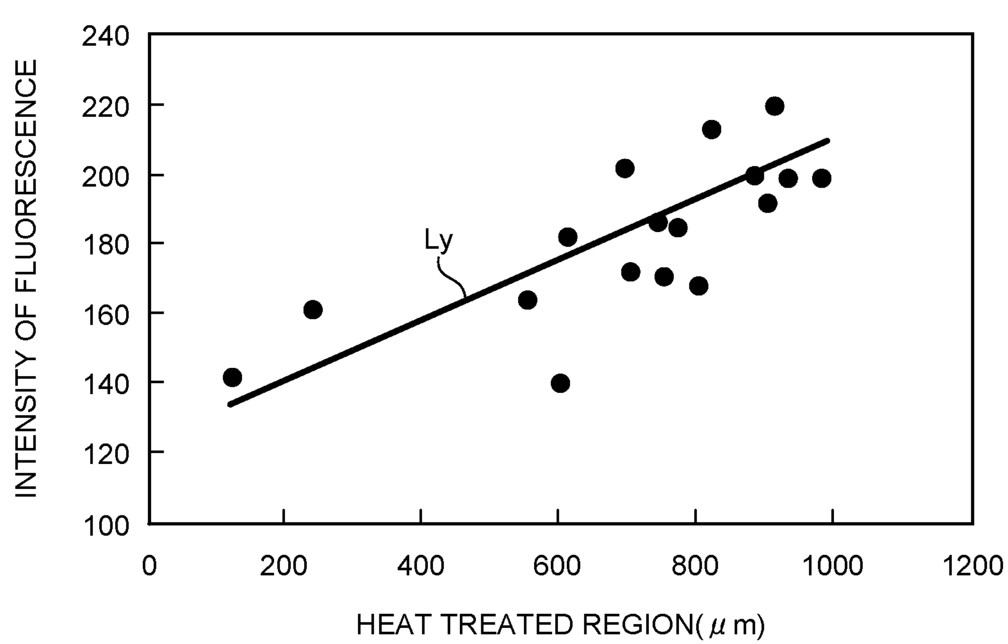
FIG. 27 is a diagram illustrating correspondence between intensity of fluorescence and depth of heat treatment.

FIG. 26 is a diagram illustrating an example of an image displayed by the display device 7. FIG. 27 is a diagram illustrating correspondence between intensity of fluorescence and depth of heat treatment. In FIG. 27, the vertical axis represents the intensity of fluorescence and the horizontal axis represents the depth of heat treatment within body tissue. Furthermore, in FIG. 27, a straight line Ly represents a correlation between the intensity of fluorescence and the depth of heat treatment within the body tissue.

Figure 28:
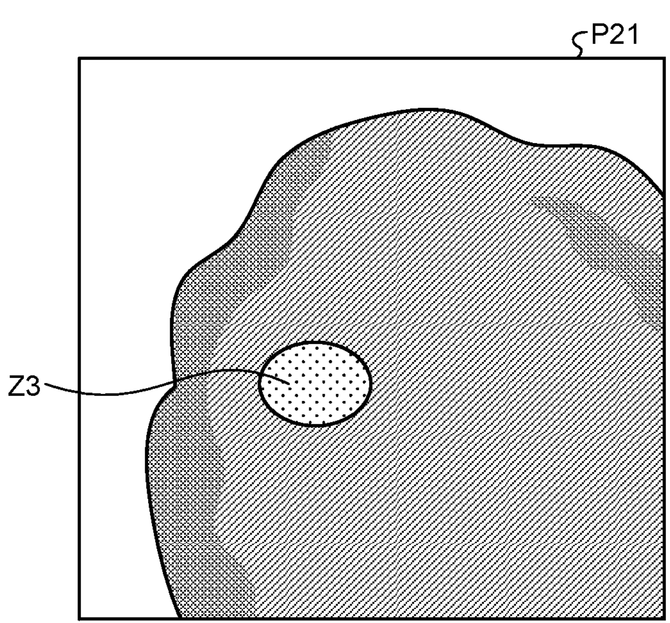
FIG. 28 is a diagram illustrating another example of the image displayed by the display device according to the second embodiment.

As illustrated in FIG. 26, the control unit 95 causes the image processing unit 92 to cause the display device 7 to display a combined image P20 that is a combination of a white image and a heat treatment image. In this case, the image processing unit 92 generates the combined image P20 by combining the white image and the heat treatment image so that a combination ratio between the white image and the heat treatment image becomes 1:1. Furthermore, as illustrated in FIG. 26 and FIG. 27, the image processing unit 92 generates the combined image P20 having a color highlight-displayed, the color being that of a fluorescent region, according to quantity of fluorescence emitted from a heat-treated region included in the heat treatment image. For example, as illustrated in FIG. 26, the image processing unit 92 generates a heat-treated region Z2 where the quantity of fluorescence emitted is small in blue and the heat-treated region Z1 where the quantity of fluorescence emitted is larger than that in the heat-treated region Z2 in green. The heat-treated region Z2 where the quantity of fluorescence emitted is small represents a region that has been marked by use of a treatment tool, such as an energy device, before excision of an abnormal region, such as a tumor, by an operating surgeon, such as a medical doctor, using an electrosurgical knife. Furthermore, as illustrated by a heat treatment image P21 in FIG. 28, the image processing unit 92 may generate a heat-treated region Z3 that has been heat-treated in yellow, correspondingly to quantity of fluorescence emitted. An operating surgeon, such as a medical doctor, is thereby able to intuitively know a state of heat treatment according to a color.

At Step S307, the control unit 95 determines whether or not an instruction signal to specify a heat treatment image as an image instructed to be displayed by the display device 7 has been input from the input unit 93. In a case where the control unit 95 determines that the instruction signal to specify a heat treatment image as an image instructed to be displayed by the display device 7 has been input from the input unit 93 (Step S307: Yes), the endoscope system 1 proceeds to Step S308 described later. On the contrary, in a case where the control unit 95 determines that the instruction signal to specify a heat treatment image as an image instructed to be displayed by the display device 7 has not been input from the input unit 93 (Step S307: No), the endoscope system 1 proceeds to Step S309 described later.

At Step S308, the control unit 95 causes the image processing unit 92 to generate a heat treatment image and to output the heat treatment image to the display device 7 and thereby causes the display device 7 to display the heat treatment image. For example, the control unit 95 causes the image processing unit 92 to generate the heat treatment image P11 in FIG. 25C described above and to output the heat treatment image P11 to the display device 7. After Step S308, the endoscope system 1 returns to the main routine in FIG. 19.

At Step S309, the control unit 95 causes the image processing unit 92 to generate a white image and to output the white image to the display device 7 and thereby causes the display device 7 to display the white image. For example, the control unit 95 causes the image processing unit 92 to generate the white image P10 in FIG. 25A described above and to output the white image P10 to the display device 7. After Step S309, the endoscope system 1 returns to the main routine in FIG. 19.

The second embodiment described above enables, by means of the single imaging element 53, both narrow band light observation and observation of fluorescence generated by heat treatment using an energy device because the cut filter 54 is provided on the light receiving surface side of the pixels provided with the filters G and the cut filter 54 shields shorter wavelength light including the wavelength band of the second narrow band light and transmits therethrough the first narrow band light.

Third Embodiment

A third embodiment will be described next. The first and second embodiments described above are each related to an endoscope system including a rigid endoscope, but with respect to the third embodiment, an endoscope system including a flexible endoscope will be described. The endoscope system according to the third embodiment will be described hereinafter. The same reference signs will be assigned to components of the third embodiment that are the same as those of the above described endoscope system 1 according to the first embodiment, and detailed description of these components will thus be omitted.

Configuration of Endoscope System

Figure 29:
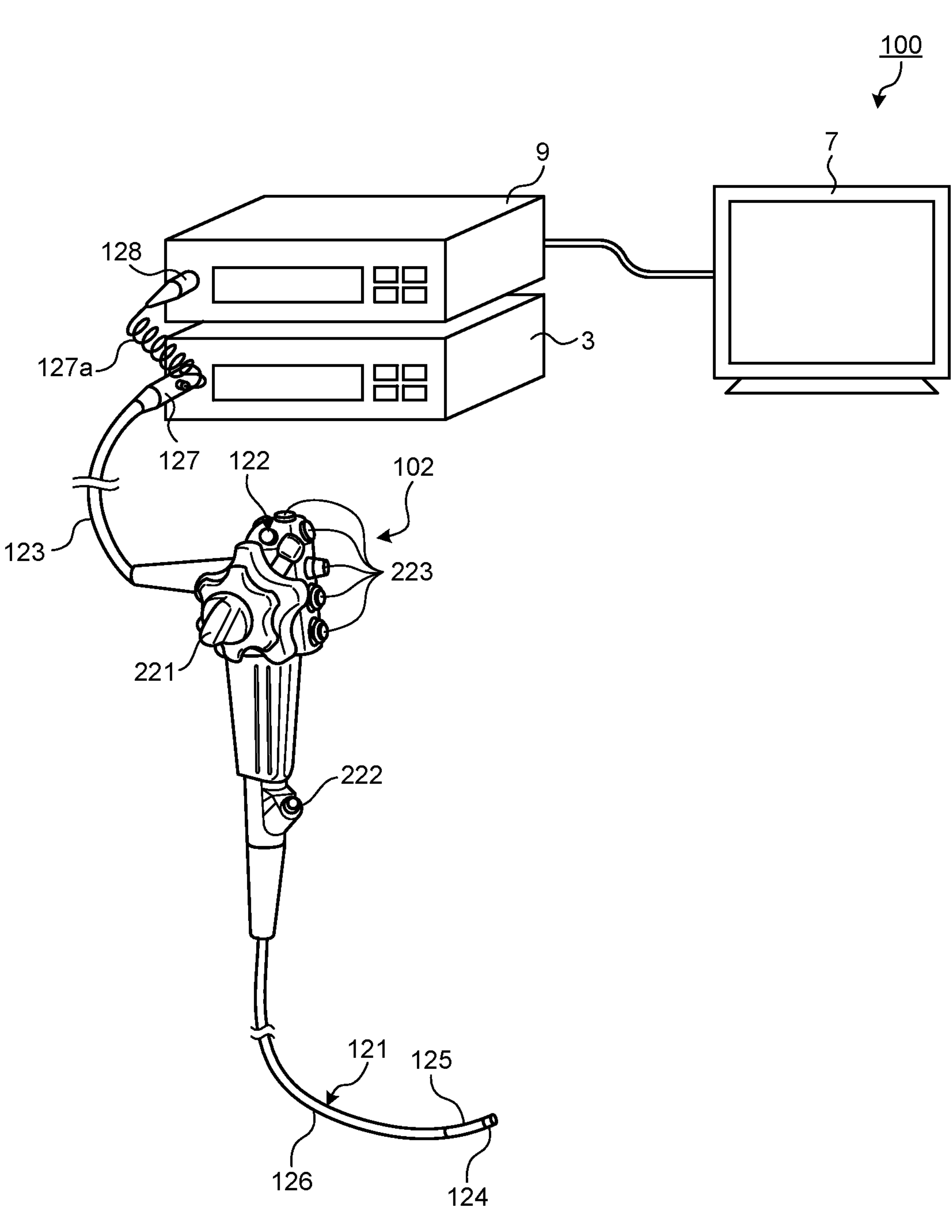
FIG. 29 is a diagram illustrating a schematic configuration of an endoscope system according to a third embodiment.
Figure 30:
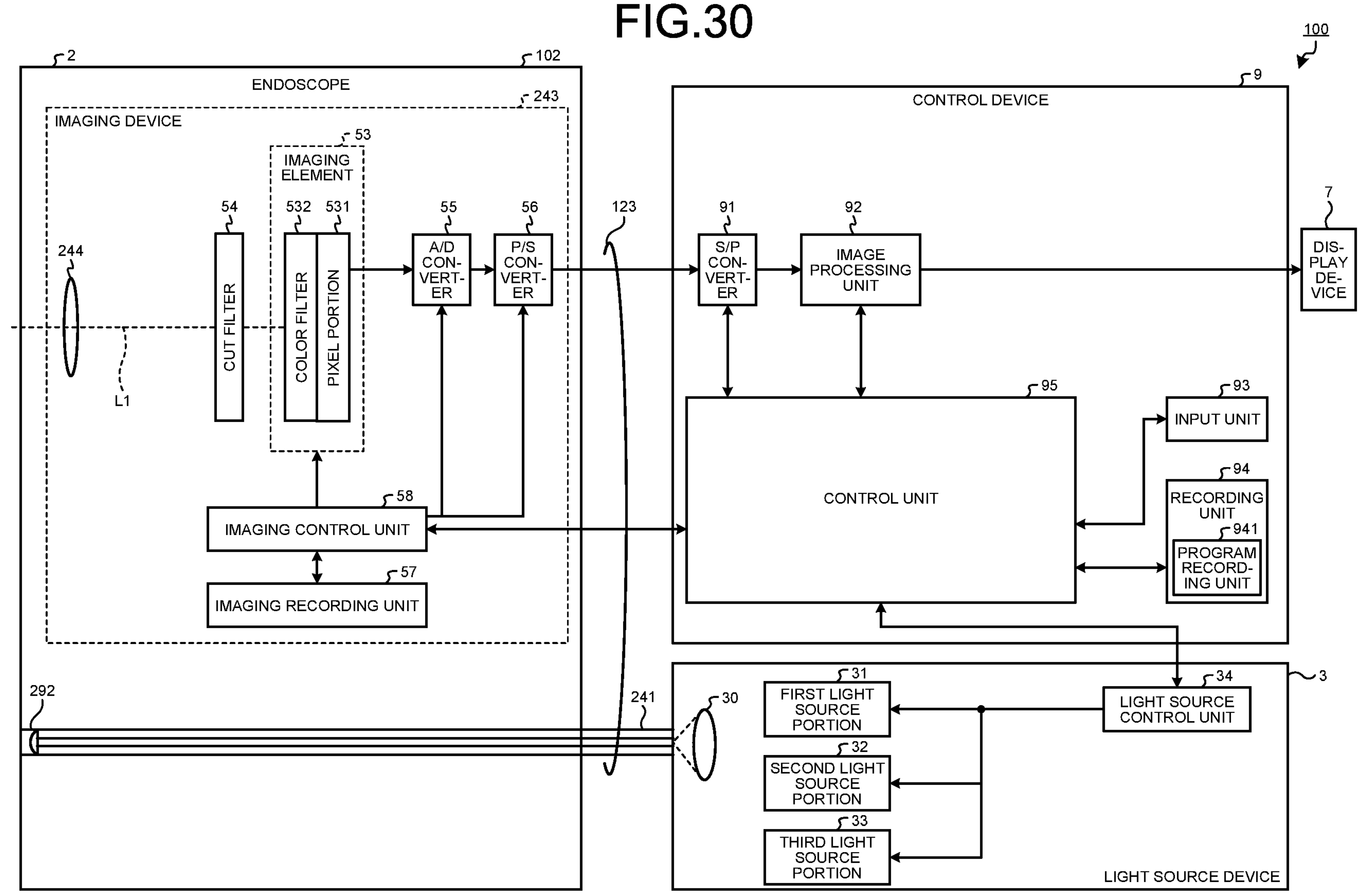
FIG. 30 is a block diagram illustrating a functional configuration of main parts of the endoscope system according to the third embodiment.

FIG. 29 is a diagram illustrating a schematic configuration of the endoscope system according to the third embodiment. FIG. 30 is a block diagram illustrating a functional configuration of main parts of the endoscope system according to the third embodiment.

In an endoscope system 100 illustrated in FIG. 29 and FIG. 30, an image of the interior of the body of a subject, such as a patient, is captured by insertion into the subject, and a display image based on data on the image captured is displayed by the display device 7. By observing the display image displayed by the display device 7, an operating surgeon, such as a medical doctor, examines any presence and/or a state of an abnormal region having a site to be examined captured therein, the site being, for example, a bleeding site, a tumor site, and/or an abnormal site. Furthermore, the operating surgeon, such as a medical doctor, performs treatment of the subject by inserting a treatment tool, such as an energy device, into the body of the subject via a treatment tool channel of an endoscope. The endoscope system 100 includes, in addition to the light source device 3, display device 7, and control device 9 described above, an endoscope 102.

Configuration of Endoscope

The following description is related to a configuration of the endoscope 102. The endoscope 102 generates image data by capturing an image of the interior of the body of a subject and outputs the image data generated, to the control device 9. The endoscope 102 includes an operating unit 122 and a universal cord 123.

An insertion portion 121 has flexibility and is elongated. The insertion portion 121 includes: a distal end portion 124 having, built therein, an imaging device described later; a bending portion 125 that includes plural bending pieces and is bendable; and a flexible tube portion 126 that is connected to a proximal end of the bending portion 125, has flexibility, and is elongated.

The distal end portion 124 is formed by use of, for example, glass fiber. The distal end portion 124 includes: a light guide 241 forming a light guiding path for light supplied from the light source device 3; an illumination lens 242 provided at a distal end of the light guide 241; and an imaging device 243.

The imaging device 243 includes an optical system 244 for condensing light, and the above described imaging element 53, cut filter 54, A/D converter 55, P/S converter 56, imaging recording unit 57, and imaging control unit 58 according to the first embodiment. In this third embodiment, the imaging device 243 functions as a medical imaging device.

The universal cord 123 has, built therein, at least the light guide 241 and an assembly cable having one or plural cables bundled together. The assembly cable includes signal lines for transmitting and receiving signals between: the endoscope 102 and light source device 3; and the control device 9. These signal lines include a signal line for transmitting and receiving setting data, a signal line for transmitting and receiving a captured image (image data), and a signal line for transmitting and receiving a driving timing signal for driving the imaging element 53. The universal cord 123 has a connector 127 that is attachable to and detachable from the light source device 3. A coil cable 127*a* that is coil-shaped extends from the connector 127. A connector 128 attachable to and detachable from the control device 9 is provided at an extended end of the coil cable 127*a*.

The endoscope system 100 configured as described above performs processing similar to that by the above described endoscope system 1 according to the first embodiment.

The third embodiment described above has effects similar to those of the first embodiment described above, and also enables reduction in diameter of the insertion portion 121 because both narrow band light observation and observation of fluorescence generated by heat treatment with an energy device are able to be conducted by means of just the single imaging element 53.

Fourth Embodiment

A fourth embodiment will be described next. Endoscope systems have been described above with respect to the first to third embodiments, but application to a surgical microscope system will be described with respect to the fourth embodiment. The same reference signs will be assigned to components of the fourth embodiment that are the same as those of the above described endoscope system 1 according to the first embodiment, and detailed description of these components will thus be omitted.

Configuration of Surgical Microscope System

Figure 31:
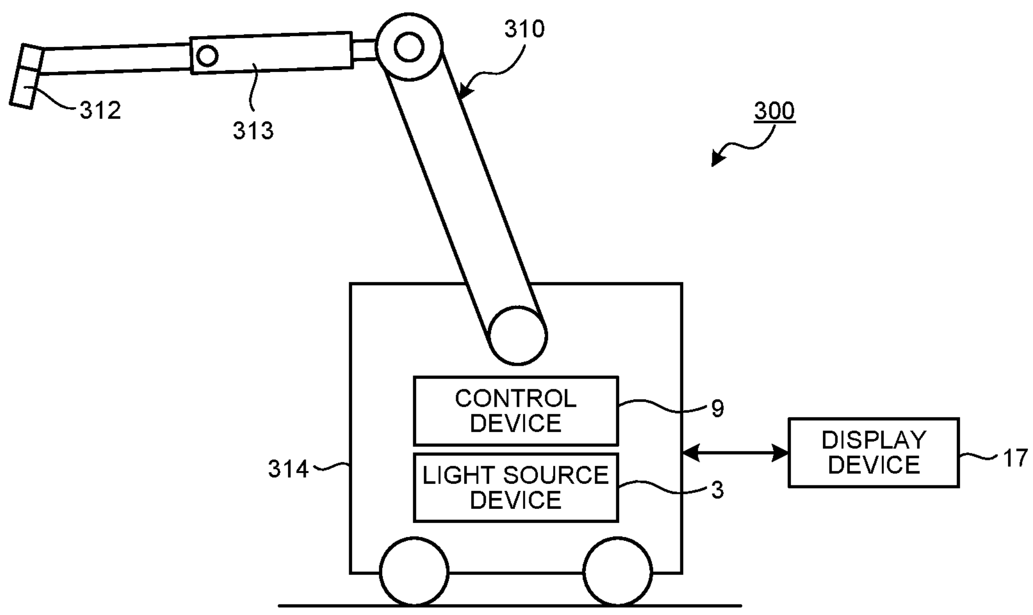
FIG. 31 is a diagram illustrating a schematic configuration of a surgical microscope system according to a fourth embodiment.

FIG. 31 is a diagram illustrating a schematic configuration of the surgical microscope system according to the fourth embodiment. A surgical microscope system 300 illustrated in FIG. 31 includes: a microscope device 310 that is a medical imaging device that obtains an image for observation of a subject by imaging; and the display device 17. The display device 17 and the microscope device 310 may be configured integrally with each other.

The microscope device 310 includes: a microscope unit 312 that captures an enlarged image of a microscopic site in a subject; a supporting unit 313 that is connected to a proximal end portion of the microscope unit 312 and includes an arm that supports the microscope unit 312 rotatably; and a base unit 314 that holds a proximal end portion of the supporting unit 313 rotatably and is capable of moving on a floor surface. The base unit 314 includes: the light source device 3 that generates, for example, white light, the first narrow band light, and the second narrow band light to be emitted to a subject from the microscope device 310; and the control device 9 that controls operation of the surgical microscope system 300. The light source device 3 and the control device 9 both have at least the same configurations as those in the first embodiment described above. Specifically, the light source device 3 includes the condenser lens 30, the first light source portion 31, the second light source portion 32, the third light source portion 33, and the light source control unit 34. The control device 9 includes the S/P converter 91, the image processing unit 92, the input unit 93, the recording unit 94, and the control unit 95. Instead of being provided movably on the floor surface, the base unit 314 may be configured to support the supporting unit 313 by being be fixed to, for example, a ceiling or a wall surface.

The microscope unit 312 is, for example, cylindrical, and includes therein the medical imaging device described above. Specifically, the medical imaging device includes the same configuration as that of the above described endoscope camera head 5 according to the first embodiment. For example, the microscope unit 312 includes the optical system 51, the drive unit 52, the imaging element 53, the cut filter 54, the A/D converter 55, the P/S converter 56, the imaging recording unit 57, and the imaging control unit 58. Furthermore, a switch that receives input of an operation instruction for the microscope device 310 is provided on a side surface of the microscope unit 312. A cover glass that protects the interior of the microscope unit 312 is provided on the plane of an opening at a lower end of the microscope unit 312.

In the surgical microscope system 300 configured as described above, the microscope unit 312 is moved, a zooming operation is performed, and/or illumination light is changed, by a user, such as an operating surgeon, while the user operates any of various switches in a state where the microscope unit 312 is being held by the user. The microscope unit 312 preferably has an elongated shape extending in an observation direction so that it is easy for the user to hold the microscope unit 312 and change the field of view direction. Therefore, the microscope unit 312 may be not cylindrical, and may have, for example, a polygonal prism shape.

The above described surgical microscope system 300 according to the fourth embodiment also achieves effects similar to those of the above described first embodiment and additionally enables downsizing of the microscope unit 312.

First Modified Example of First to Fourth Embodiments

A first modified example of the first to fourth embodiments will be described next. Only a configuration of a cut filter in the first modified example of the first to fourth embodiments is different from those of the first to fourth embodiments. The configuration of the cut filter according to the first modified example of the first to fourth embodiments will thus be described hereinafter.

Figure 32:
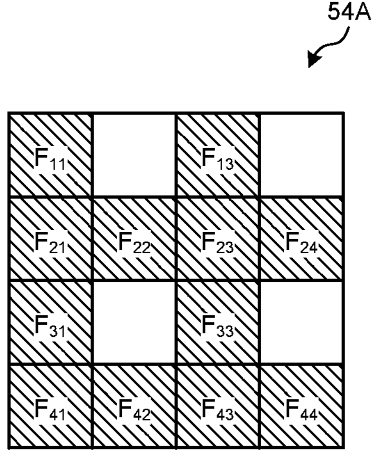
FIG. 32 is a diagram schematically illustrating a configuration of a cut filter according to a first modified example of the first to fourth embodiments.

FIG. 32 is a diagram schematically illustrating the configuration of the cut filter according to the first modified example of the first to fourth embodiments. A cut filter 54A illustrated in FIG. 32 is provided on the light receiving surface side (incident surface side) of at least the G pixels provided with the filters G of the color filter 532 and on the light receiving surface side (incident surface side) of the R pixels provided with the filters R of the color filter 532, shields light of a short wavelength band including the wavelength band of the second narrow band light, and transmits therethrough light that includes the first narrow band light and that is light of a wavelength band longer than the wavelength band of the second narrow band light. Specifically, as illustrated in FIG. 32, a filter $F_{11}$ forming the cut filter 54A is arranged at a position where the filter $G_{11}$ is arranged (see FIG. 5) and on the light receiving surface side directly above the filter $G_{11}$. Furthermore, a filter $F_{21}$ is arranged at a position where the filter $R_{21}$ is arranged (see FIG. 5) and on the light receiving surface side directly above the filter $R_{21}$.

Method of Manufacturing Cut Filter

Figure 33A:
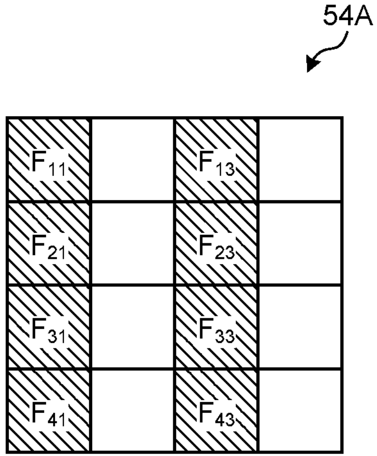
FIG. 33A is a diagram schematically illustrating a method of manufacturing the cut filter according to the first modified example of the first to fourth embodiments.
Figure 33B:
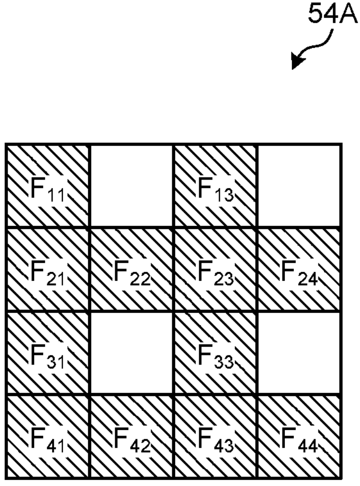
FIG. 33B is a diagram schematically illustrating the method of manufacturing the cut filter according to the first modified example of the first to fourth embodiments.

A method of manufacturing the cut filter 54A will be described next. FIG. 33A and FIG. 33B are diagrams schematically illustrating the method of manufacturing the cut filter 54A.

As illustrated in FIG. 33A, firstly, a coating device (not illustrated in the drawings) that coats an object with a light-shielding film coats rows in the cut filter 54A with a light-shielding film, the rows corresponding to rows of G pixels and R pixels arranged along a vertical direction of the cut filter 54A (FIG. 33A). Subsequently, the coating device coats rows in the cut filter 54A with a light-shielding film, the rows corresponding to rows of G pixels and R pixels arranged along a horizontal direction of the cut filter 54A (FIG. 33B).

The above described first modified example of the first to fourth embodiments facilitates connection of the cut filter 54A.

Furthermore, in the above described first modified example of the first to fourth embodiments, the coating process is performed twice in the vertical direction and the horizontal direction, but, for example, the cut filter 54A may be manufactured by masking portions corresponding to the B pixels, coating the entire surface with a light-shielding film, and thereafter removing the mask.

Second Modified Example of First to Fourth Embodiments

A second modified example of the first to fourth embodiments will be described next. In the second modified example of the first to fourth embodiments, the above described cut filter 54 according to the first embodiment has been omitted and transmission characteristics of filters G of a color filter have been made different. A configuration of the color filter according to the second modified example of the first to fourth embodiments will thus be described hereinafter. The same reference signs will be assigned to components of the second modified example of the first to fourth embodiments, the components being the same as those of the above described endoscope system 1 according to the first embodiment, and detailed description of these components will thus be omitted.

Figure 34:
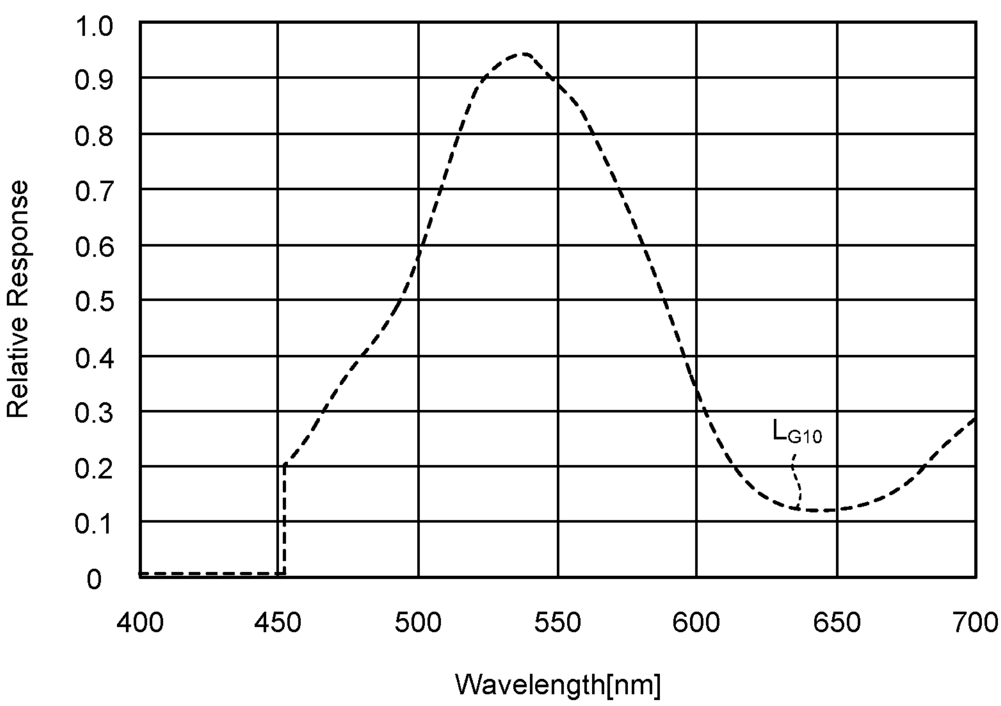
FIG. 34 is a diagram schematically illustrating transmission characteristics of a filter G of a color filter according to a second modified example of the first to fourth embodiments.

FIG. 34 is a diagram schematically illustrating the transmission characteristics of the filters G of the color filter according to the second modified example of the first to fourth embodiments. In FIG. 34, the horizontal axis represents wavelength and the vertical axis represents the transmission characteristics. In FIG. 34, a curve $L_{G10}$ represents the transmission characteristics of the filters G.

As represented by the curve $L_{G10}$ in FIG. 34, the filters G shield light of a wavelength band shorter than 415 nm. That is, the filters G shield light of a short wavelength band including the wavelength band of the second narrow band light and transmit therethrough light that includes the first narrow band light and that is light of a wavelength band longer than the wavelength band of the second narrow band light.

The above described second modified example of the first to fourth embodiments enables the cut filter 54 to be omitted and thus enables the configuration to be uncomplicated.

Third Modified Example of First to Fourth Embodiments

A third modified example of the first to fourth embodiments will be described next. A cut filter in the third modified example of the first to fourth embodiments has a configuration different from that of the above described cut filter 54 according to the first embodiment. The configuration of the cut filter according to the third modified example of the first to fourth embodiments will thus be described hereinafter. The same reference signs will be assigned to components of the third modified example of the first to fourth embodiments, the components being the same as those of the above described endoscope system 1 according to the first embodiment, and detailed description of these components will thus be omitted.

Figure 35:
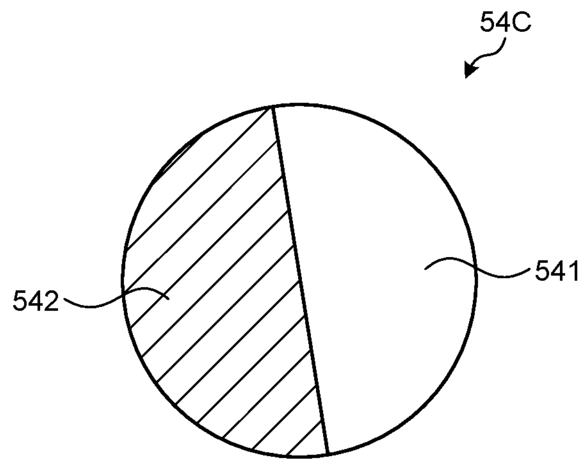
FIG. 35 is a diagram schematically illustrating a configuration of a cut filter according to a third modified example of the first to fourth embodiments.

FIG. 35 is a diagram schematically illustrating the configuration of the cut filter according to the third modified example of the first to fourth embodiments. A cut filter 54C illustrated in FIG. 35 has a transmitting portion 541 that is disk-shaped and transmits therethrough light of all wavelength bands, and a transmitting portion 542 that shields light of a short wavelength band including the wavelength band of the second narrow band light and transmits therethrough light that includes the first narrow band light and that is light of a wavelength band longer than the wavelength band of the second narrow band light. The cut filter 54C is rotated about the optical axis L1 by a drive unit, such as a motor, not illustrated in the drawings.

The above described third modified example of the first to fourth embodiments achieves effects similar to those of the above described first to fourth embodiments.

Furthermore, in the third modified example of the first to fourth embodiments, the wavelength band of light incident on the imaging element 53 is limited by rotation of the cut filter 54C, but, for example, an electronic filter that shields light of a predetermined wavelength band according to an electric current value may be provided instead of the cut filter 54C.

OTHER EMBODIMENTS

Various embodiments may be formed by combination, as appropriate, of plural components disclosed with respect to the above described medical observation systems according to the first to fourth embodiments of the present disclosure. For example, some of the components described with respect to the medical observation system/systems according to any of the above described embodiments of the present disclosure may be eliminated. Furthermore, any components described with respect to the medical observation system/systems according to any of the above described embodiments of the present disclosure may be combined as appropriate.

Furthermore, the "units" described above with respect to the medical observation systems according to the first to fourth embodiments of the present disclosure may be read as "means" or "circuits". For example, the control unit may be read as a control means or a control circuit.

In the description of the flowcharts in this specification, the context of the processing among the steps is disclosed by use of expressions, such as "firstly", "thereafter", and "subsequently", but sequences in the processing needed for implementation of the disclosure are not uniquely defined by these expressions. That is, the sequences in the processing in the flowcharts described in this specification may be modified as far as no contradiction arises from the modification.

Some of embodiments of the present application have been described hereinbefore in detail on the basis of the drawings, but these are just examples. The disclosure may be implemented in various other modes modified or improved on the basis of the modes described through the present disclosure and knowledge of those skilled in the art.

The present disclosure achieves an effect of enabling both narrow band light observation and fluorescence observation by means of a single imaging element.

What is claimed is:

1. A medical observation system comprising:

a light source configured to emit, to body tissue:

first narrow band light, wherein a wavelength band of the first narrowband light is narrower than a wavelength band of white light, and second narrow band light, wherein a wavelength band of the second narrow band light is shorter than the wavelength band of the first narrow band light, and the wavelength band of the second narrow band light is configured to excite an advanced glycation end product, wherein the light source is configured to be controlled to emit the second narrow band light, and to selectively emit the first narrow band light with the second narrow band light;

an imaging element comprising:

plural pixels arranged in a two-dimensional matrix; and a color filter comprising red filters, green filters, and blue filters that are provided on corresponding light receiving surfaces of the plural pixels, wherein the imaging element is configured to generate image data by imaging at least one of returned light from the body tissue and fluorescence from the advanced glycation end product; and a cut filter provided on a light receiving surface side of first pixels of plural pixels provided with the green filters, the cut filter being configured to:

shield light having a wavelength band comprising the wavelength band of the second narrow band light; and transmit therethrough light having a wavelength band comprising the wavelength band of the first narrow band light, wherein the cut filter is not provided on a light receiving surface side of second pixels of the plural pixels provided with the blue filters.

2. The medical observation system according to claim 1, further comprising:

a processor comprising hardware, the processor being configured to:

generate a narrow band light image based on first blue component signals from the pixels where the blue filters are arranged and on first green component signals from the pixels where the green filters are arranged, the first blue component signals and the first green component signals being included in the image data when the first narrow band light and the second narrow band light have been emitted to the body tissue from the light source; and generate a heat treatment image based on second blue component signals from the pixels where the blue filters are arranged and on second green component signals from the pixels where the green filters are arranged, the second blue component signals and the second green component signals being included in the image data when only the second narrow band light has been emitted to the advanced glycation end product from the light source.

3. The medical observation system according to claim 2, wherein the processor is configured to make gains for the second blue component signals smaller than gains for the second green component signals when only the second narrow band light has been emitted to the advanced glycation end product from the light source.

4. The medical observation system according to claim 2, wherein the processor is configured to adjust gains for the second blue component signals and gains for the second green component signals such that a ratio between the second blue component signals and the second green component signals becomes constant when only the second narrow band light has been emitted to the advanced glycation end product from the light source.

5. The medical observation system according to claim 2, wherein:

the light source is further configured to emit white light; and the processor is configured to adjust white balance to generate a white image such that a ratio of values of a red component signal, a green component signal, and a blue component signal included in the image data when the white light has been emitted to the body tissue from the light source becomes constant.

6. The medical observation system according to claim 1, wherein the fluorescence has a wavelength band of 500 nm to 640 nm.

7. The medical observation system according to claim 1, wherein:

the first narrow band light has a wavelength band of 530 nm to 550 nm;

the second narrow band light has a wavelength band of 390 nm to 430 nm; and the cut filter is configured to shield light having a wavelength shorter than 430 nm.

8. The medical observation system according to claim 1, further comprising an energy device configured to perform a heat treatment on the body tissue to generate the advanced glycation end product.

9. The medical observation system according to claim 1, further comprising:

an insertion portion configured to be inserted into a subject, the insertion portion comprising an optical system configured to condense the returned light and the fluorescence; and a medical imaging device comprising the imaging element and the cut filter, wherein the insertion portion is attachable to and detachable from the medical imaging device.

10. The medical observation system according to claim 1, further comprising:

an endoscope comprising an insertion portion comprising a distal end portion configured to be inserted into a subject; and a medical imaging device provided in the distal end portion, the medical imaging device comprising the imaging element and the cut filter.

11. The medical observation system according to claim 1, further comprising:

a medical imaging device;

a support configured to support the medical imaging device rotatably; and a base configured to hold a proximal end portion of the support rotatably, the base being configured to move on a floor surface, wherein the medical imaging device comprises the imaging element and the cut filter.

12. A medical observation system comprising:

a light source configured to selectively emit:

in a narrow band light observation mode, first blue light to illuminate body tissue, wherein the first blue light is selected to be absorbed by hemoglobin in blood relative to other lights, and easily reflected by a mucosal surface layer relative to other lights; and in a heat treatment observation mode, second blue light to illuminate the body tissue, wherein the second blue light is selected to excite an advanced glycation end product generated by performing a heat treatment on the body tissue;

an imaging element to be commonly used in the narrow band light observation mode and the heat treatment observation mode, the imaging element comprising:

plural pixels arranged in a two-dimensional matrix; and a color filter comprising red filters, green filters, and blue filters provided on corresponding light receiving surfaces of the plural pixels;

wherein the imaging element is configured to generate image data by imaging at least one of returned light from the body tissue and fluorescence from the advanced glycation end product; and a cut filter provided on a light receiving surface side of first pixels of the plural pixels provided with the green filters, the cut filter being configured to:

transmit therethrough light of a wavelength band comprising a wavelength band of the fluorescence, and shield the first blue light and the second blue light, wherein the cut filter is not provided on a light receiving surface side of second pixels of plural pixels provided with the blue filters.

13. The medical observation system according to claim 12, wherein the first blue light and the second blue light are generated from a single light source portion.

14. The medical observation system according to claim 13, further comprising:

a processor comprising hardware, the processor being configured to:

generate a narrow band light image based on first blue component signals from the pixels where the blue filters arranged, the first blue component signals being included in the image data when the first blue light has been emitted to the body tissue from the light source in the narrow band light observation mode; and generate a heat treatment image based on second blue component signals from the pixels where the blue filters are arranged and on green component signals from the pixels where the green filters are arranged, the second blue component signals and the green component signals being included in the image data when only the second blue light has been emitted to the advanced glycation end product from the light source in the heat treatment observation mode.

* * * * *